US008612018B2

(12) United States Patent
Gillbe

(10) Patent No.: US 8,612,018 B2
(45) Date of Patent: Dec. 17, 2013

(54) ARRAY STIMULATOR

(76) Inventor: Ivor Stephen Gillbe, Bristol (GB)

( * ) Notice: Subject to any disclaimer, the term of this patent is extended or adjusted under 35 U.S.C. 154(b) by 986 days.

(21) Appl. No.: 12/601,036

(22) PCT Filed: May 20, 2008

(86) PCT No.: PCT/GB2008/001723
§ 371 (c)(1),
(2), (4) Date: Nov. 20, 2009

(87) PCT Pub. No.: WO2008/142402
PCT Pub. Date: Nov. 27, 2008

(65) Prior Publication Data
US 2010/0152817 A1 Jun. 17, 2010

(30) Foreign Application Priority Data
May 22, 2007 (GB) .................................. 0709834.6

(51) Int. Cl.
A61N 1/36 (2006.01)
(52) U.S. Cl.
USPC ............................................................ 607/72
(58) Field of Classification Search
USPC ........................................ 607/72, 67, 70, 117
See application file for complete search history.

(56) References Cited

U.S. PATENT DOCUMENTS

| | | | |
|---|---|---|---|
| 2,622,601 A | 12/1952 | Nemec | |
| 3,096,768 A | 7/1963 | Griffith, Jr. | |
| 3,646,940 A | 3/1972 | Timm et al. | |
| 4,379,462 A | 4/1983 | Borkan et al. | |
| 4,813,418 A | 3/1989 | Harris | |
| 5,069,211 A | 12/1991 | Bartelt et al. | |
| 5,165,404 A * | 11/1992 | Andersson et al. | 607/2 |
| 5,324,317 A * | 6/1994 | Reiss | 607/67 |
| 5,417,719 A | 5/1995 | Hull et al. | |
| 5,713,922 A | 2/1998 | King | |
| 5,776,170 A | 7/1998 | MacDonald et al. | |
| 5,948,007 A * | 9/1999 | Starkebaum et al. | 607/67 |
| 6,181,969 B1 | 1/2001 | Gord | |
| 6,505,078 B1 * | 1/2003 | King et al. | 607/67 |
| 6,516,227 B1 | 2/2003 | Meadows et al. | |
| 6,584,358 B2 * | 6/2003 | Carter et al. | 607/69 |
| 6,684,104 B2 | 1/2004 | Gordon et al. | |
| 6,909,917 B2 | 6/2005 | Woods et al. | |
| 7,054,686 B2 | 5/2006 | MacDonald | |

(Continued)

FOREIGN PATENT DOCUMENTS

EP 0414248 A3 8/1990
GB 2414410 A 11/2005

(Continued)

Primary Examiner — Christopher D Koharski
Assistant Examiner — Jeremiah Kimball
(74) Attorney, Agent, or Firm — McGarry Bair PC

(57) ABSTRACT

An array stimulator has a plurality of electrodes in an array, the electrodes forming a plurality of electrode pairs, and a signal generator for generating signals to the electrodes so as to generate electrical pulse in a patient to which the stimulator has been applied either transcutaneously or by implantation. Those electrical pulses form a composite pulse in the patient which stimulates the nervous system of the patient. The composite pulse has a duration between 4 μs and 1500 μs and a maximum voltage between 2V and 50V when the stimulator is implanted, and 15V to 500V when applied transcutaneously. The electrical pulses themselves are significantly shorter duration than the composite pulse, so they stimulate the nervous system of the patient much less than the composite pulse or not at all.

24 Claims, 18 Drawing Sheets

(56) References Cited

U.S. PATENT DOCUMENTS

| | | | |
|---|---|---|---|
| 7,212,867 B2 * | 5/2007 | Van Venrooij et al. | 607/116 |
| 7,228,178 B2 * | 6/2007 | Carroll et al. | 607/45 |
| 2003/0120323 A1 | 6/2003 | Meadows et al. | |
| 2003/0139781 A1 | 7/2003 | Bradley et al. | |
| 2004/0034394 A1 | 2/2004 | Woods et al. | |
| 2006/0015153 A1 * | 1/2006 | Gliner et al. | 607/45 |
| 2006/0149337 A1 * | 7/2006 | John | 607/45 |
| 2007/0073354 A1 | 3/2007 | Knudson et al. | |
| 2010/0261994 A1 * | 10/2010 | Davalos et al. | 600/411 |

FOREIGN PATENT DOCUMENTS

| | | |
|---|---|---|
| WO | 9830280 A1 | 7/1998 |
| WO | 2005115536 A | 12/2005 |
| WO | 2005115536 A1 | 12/2005 |
| WO | 2006045397 A1 | 5/2006 |
| WO | 2008012523 A | 1/2008 |
| WO | 2008012523 A2 | 1/2008 |

* cited by examiner

ARRAY STIMULATOR

CROSS-REFERENCE TO RELATED APPLICATIONS

This application claims priority on International Application No. PCT/GB2008/001723, filed May 20, 2008 and GB0709834.6 filed May 22, 2007, both of which are incorporated herein by reference in its entirety.

FIELD OF THE INVENTION

The present invention relates to an electrical device designed to produce currents that affect the behaviour of nerves and other excitable tissues lying at various distances from the electrodes and provides apparatus and methods for application of such device.

BACKGROUND OF THE INVENTION

Electrical stimulation of nerves has been in use for therapeutic purposes for more than 40 years.

For example Melzack and Wall 1965 described how analgesia could be produced when Aβ nerve fibres are stimulated at 100 Hz, a frequency that none of the other afferent fibres can follow faithfully. Wall 1986 produced these effects by applying the current through needles inserted into the patient's nerves. To avoid possible complications of inserting needles, he soon employed surface electrodes, leading to the term Transcutaneous Electrical Nerve Stimulation (TENS).

A typical TENS machine develops a pulse whose width can be varied from 50-250 μs, employing a current whose amplitude can be increased from 0-50 mA, and whose frequency is in the range of 1 to 250 Hz. The pulse width is sufficiently long in duration to excite Aβ fibres at low voltage causing a painless tingling and stimulation of interneurones releasing GABA. Johnson et al 1991 showed that 'high intensity stimulation', where the amplitude is increased sufficiently to recruit Aδ fibres, invokes release of met-enkephalin in the spinal cord which produces a more prolonged analgesic effect than that provided by the release of GABA produced by the more usual 'low intensity stimulation' of Aβ fibres. Salar et al 1981 observed that opioids were released slowly into the cerebrospinal fluid when TENS is performed at frequencies of 40-60 Hz and at amplitudes of 40-80 mA, signals that readily recruit Aδ fibres and whose firing is associated with sharp pain.

It is generally believed that TENS analgesia is caused mainly by cutaneous afferent fibre activation. However, Radkarishnan et al 2005 demonstrated that by differentially blocking cutaneous and deep tissue primary afferents, activation of large diameter primary afferents from deep somatic tissues, and not cutaneous afferent fibres, are pivotal in causing TENS analgesia.

A potential limitation of the effectiveness of TENS stimulation may therefore be that intensity of stimulation is limited by pain arising from activation of Aδ and C-fibres lying immediately under the electrodes.

As tissue impedance is capacitive, impedance tends to fall as frequency is increased. In order to increase tissue penetration, signals may be provided at a frequency where the intervals between each electric signal are less than the refractory periods of fibres that require stimulation. In order to produce action potentials, such signals are modulated to provide low frequency stimulation either by interference or interruption.

The interference method of applying medium frequency currents is exemplified by Nemec U.S. Pat. No. 2,622,601 "Electrical Nerve Stimulator", Griffith U.S. Pat. No. 3,096,768 "Electrotherapy System" (Firmtron Inc) and many others. Two signal sources are each connected to a pair of electrodes. They can produce an amplitude modulated medium frequency signal in the tissues called interferential current, as follows. The first signal source uses a medium frequency carrier wave (typically 4.0 kHz) while the other operates at a slightly different frequency (typically 4.1 kHz). Their respective pairs of surface electrodes are arranged on the body in a manner that allows the two oscillating currents to intersect in deep tissues where interference is produced at a beat frequency in the low frequency range, typically at 100 Hz. This in turn is said to stimulate deeply placed Aβ fibres to produce analgesia.

However, there has been controversy as to whether or not a beat frequency is required to cause action potentials. Palmer et al 1999 discovered that when there is no interference frequency, i.e. the patient is receiving currents from both signal generators at 4 kHz and this frequency is no longer subjected to amplitude modulation, sensation still occurs. Moreover, the threshold of sensation generated in this way at 4 kHz takes place at lower amplitude than that produced by low frequency signals at less than 100 Hz. Signals administered at a frequency higher than any individual fibre can respond to on a 1:1 basis will produce asynchronous volleys in a nerve trunk as a result of action potentials arising in any axons in the vicinity of the next signal that by coincidence are no longer refractory.

Another method of improving tissue penetration in transcutaneous stimulation devices is described in Carter and Siff U.S. Pat. No. 7,130,696 "Percutaneous electrode array" in which the electrode is constructed from an array of microscopic pins that are intended to penetrate the outer layers of the skin thereby overcoming the electrical impedance of these layers.

Macdonald and Coates U.S. Pat. No. 5,776,170 "Electrotherapeutic apparatus" (1995) explored the effects of applying electric signals whose pulse width is so brief, typically 4 μs, that the voltage gated channels lying in excitable membranes of peripheral fibres that lie in the path of the current do not have time to respond to these signals sufficiently to reach membrane threshold and produce action potentials. This form of electrotherapy produces analgesic and mood altering effects provided that surface electrodes are placed over the spinal cord. Macdonald and Coates 1995 called this method TSE (Transcutaneous Spinal Electroanalgesia).

Littlewood et al GB2414410 "Electrotherapy Apparatus" (Bioinduction Ltd, 2005) discusses the effects of employing short high power electrotherapy waveforms for therapeutic purposes and describes the relationship between pulse width and the generation of action potentials and shows that the current in the tissues may be controlled independently of the level of sensation perceived by the patient.

Although the TENS method is reasonably well accepted by patients, it tends to produce a rather short-lived, localized region of pain relief. This is perhaps because of the aforementioned limitation on stimulation intensity caused by pain at the site of the electrodes and also because each electrode probably stimulates only those Aβ fibres that lie in the immediate vicinity of the electrodes. Accordingly, in patients where there is pain in several areas of the body, there is a need to improve the method, to produce a more long-lasting and generalized form of pain relief.

In 1967 in order to activate more Aβ fibres, electrodes were implanted by Professor Norman Shealy (Shealy et al 1967, 1971) in the spinal canal to stimulate the central nervous system, in particular the dorsal column (tracts through which the Aβ fibres pass up and down the spinal cord). Now termed Spinal Cord Stimulation (SCS), a repetitive low frequency pulse is employed typically at a frequency of 100 Hz or less and a pulse width in excess of 50 μs. When SCS is effective, a tingling sensation (paraesthesia) is perceived in the painful region of the body.

Since the invention of SCS by Shealy, many advances have been made in implanted devices for controlling chronic pain by means of electrical stimulation. The application of such devices has also been extended to include implanted deep brain stimulation, for pain relief and also to treat a range of conditions, for example Parkinson's disease.

Whereas transcutaneous stimulators tend to use only a few electrodes, often one or two pairs, implanted stimulators with four, eight or more pairs of electrodes are well known in the art. An early example, Timm and Bradley U.S. Pat. No. 3,646,940 "Implantable Electronic Stimulator Electrode and Method" (1969) described an apparatus for stimulation of muscles which includes a plurality of electrodes wherein a timed sequence of stimulating pulses is applied to the electrodes such that secondary tissue stimulation (that caused by current flowing between nearby electrode pairs) is eliminated.

For convenience, multiple electrode contacts are often combined on a single carrier and these arrays of electrodes are widely used today in spinal cord stimulators. For example, Borkan Savino and Waltz "Multi-electrode catheter assembly for spinal cord stimulation" U.S. Pat. No. 4,379,462 (Neuromed Inc, 1980) describes a linear array of four electrodes spaced in-line along the exterior of a catheter electrode assembly. An advantage of this type of electrode is that it is easy to insert in into the epidural space by means of a needle. These electrodes are referred to today by the term "Percutaneous electrode" because of the introduction method used.

Today percutaneous electrodes with eight contacts are often employed and two may be inserted into the epidural space, connected to a sixteen output stimulator. The surgeon programs different combinations of electrodes via wireless telemetry to stimulate a particular region of tissue in order to produce the desired therapeutic result. An array of electrodes also provides a degree of protection against migration, as it may be possible to reconfigure the electrode combination to compensate for small movements in the implanted array, to continue to stimulate a particular target area of tissue without a surgical procedure.

Another typical lead configuration is described in Hull Cross and Langley "Method of using a spinal cord stimulation lead" U.S. Pat. No. 5,417,719 (Medtronic Inc, 1993). This describes a type of "paddle electrode" so called because of the shape of the end of the lead which contains an array of electrodes located on the lead paddle. Each electrode is independently selectable such that the spinal cord may be stimulated as required.

Recent developments have attempted to increase the ability of the surgeon and/or patient to stimulate a particular area of tissue. Gord "Programmable current output stimulus stage for implantable device" U.S. Pat. No. 6,181,969 (Advanced Bionics Inc, 1999) describes a programmable output current source for use within an implantable stimulator, wherein for example sixteen individual current sources may be employed to control the flow of current in an array of electrodes. Woods et al "Implantable generator having current steering means" U.S. Pat. No. 6,909,917 (Advanced Bionics Inc, 2003) describes a means of determining a desired electrode stimulation pattern by way of a directional programming technique that translates the movement for instance of a joystick into current levels on an array of electrodes. An objective of this technique is to provide fine control over the region of tissue that is stimulated, beyond that provided by the physical locations of the individual electrodes. A disadvantage is the complexity of the stimulator device, having sixteen current controlled outputs, and the relatively poor efficiency at mid range current output which is typical of a linear electronic design, thereby compromising battery life of the implant.

There also exists in the prior art the use of pulse width modulation as a technique which has been applied across many power electronic applications in order to improve efficiency. For example MacDonald "Pulsewidth Electrical Stimulation" U.S. Pat. No. 7,054,686 (Biophan Technologies Inc, 2002) describes an apparatus that employs a series of individual pulses to improve efficiency in (for example) cardiac pacing.

SUMMARY OF THE INVENTION

In order to generate action potentials in afferent fibres, a stimulator apparatus must produce a pulse or pulses of sufficient duration and amplitude. The required amplitude to cause an action potential varies depending on the electrode arrangement and also upon the quality of contact between the electrode and the tissues. The amplitude may be expressed in terms of voltage, current, charge or energy. Electrodes may be applied to the skin or implanted, but regardless of the contact method employed, the minimum amplitude of a pulse that will activate afferent nerves declines as pulse width is increased.

According to this invention, an apparatus consisting of a pulse generator Connected to an array of electrodes is attachable to a patient's skin or implanted in the body so that it may be used to stimulate or otherwise affect the behaviour of a region of nerve or other excitable tissue. The electrodes of the electrode array, or a subset of the electrodes thereof, are excited for short durations in turn so that the current flowing from each electrode into its immediately adjacent tissue is of short duration. In the target region of tissue covered by the array or subset thereof, these short duration "component pulses" sum in turn to form a longer duration (or higher amplitude) stimulus pulse referred to as the "composite pulse".

DEFINITIONS

In this text, the following definitions apply:

Electrode—a conductive element that is used to apply electrical current to the tissues, applied either to the skin or implanted in the body.

Electrode array—a plurality of electrodes optionally including the conductive enclosure of an implanted device.

Electrode pair—the combination of one anode and one cathode (which may reverse in the case of a biphasic waveform) across which an electrical stimulus is applied. The anode and cathode are each formed from one or more electrodes from the array, in the case of more than one electrode forming either anode or cathode, these electrodes being electrically connected together. Individual electrodes may be shared between anodes or cathodes in one or more electrode pairs, provided each combination is unique.

Pulse—a single departure from the zero volt or zero amp line, ideally with rapid rising and falling edges and preferably of approximately rectangular form.

Composite pulse—the desired form of pulse used for stimulating nerves or otherwise affecting the behaviour of excitable tissues which is intended to be sub-divided into a number of sequential component parts before application to electrode pairs, typically of total duration between 4 µs and 1500 µs, or more preferably between 20 µs and 1000 µs.

Component pulse—a pulse which corresponds to a subdivision of the composite pulse, for application to a particular electrode pair, typically of maximum duration of 2 µs, or 4 µs, or 10 µs, or 20 µs, or 50 µs. The sum of the width of all component pulses should be equal to the width of the composite pulse, although where component pulses are applied with spaces between them or overlapping, the total time taken to deliver all component pulses may not be the same as the composite pulse width.

Sub-component pulse—a further subdivision of the component pulse corresponding to a train of shorter pulses for application to a particular electrode pair, to be applied either in sequence or interleaved with sub-component pulses applied to other electrode pairs.

Modulation—reduction of the pulse width of a component or sub-component pulse expressed as a percentage of the time available for that pulse derived by division of the composite pulse into the appropriate component parts.

Duty cycle—the duration or pulse width of the component pulse (or sum of the sub-component pulse widths thereof) as a proportion of the pulse width of the composite pulse.

Waveform—a combination of one or more composite pulses, component pulses or sub-component pulse trains into a pattern normally consisting of forward and reverse elements which is intended to be repeated regularly.

Cycle—the combination of all waveforms applied to a particular array intended to be repeated regularly, typically at between 0.5 Hz and 2,000 Hz or 10,000 Hz.

In one aspect, the invention is an apparatus for applying electrical pulses to a patient, the apparatus comprising a plurality of electrodes arranged in an array, and a signal generator for generating signals to said electrodes so as to form said electrical pulses, the signal generator being arranged to generate said signals such that the signals are either sequentially transmitted to said successive electrode pairs in a cycle so the respective electrode pairs receive the corresponding signals at different times, or alternatively so that the signals are received by the electrode pairs such that they do not all start and end at the same point in time, further a composite pulse that is generatable by said electrodes due to said signals has a duration between 4 µs and 1500 µs, or more preferably between 20 µs and 1000 µs, and a maximum voltage as follows:

a) for implanted devices a maximum voltage between 2 V and 50 V, or more preferably between 5V and 20V or even more preferably between 10 V and 15 V;

b) for transcutaneous devices a maximum voltage between 15V and 500V, or more preferably between 50V and 250V.

In a preferred embodiment, the composite pulse is generated by signals sequentially applied to the electrodes which are either single pulses or pulse trains with a minimum pulse width of 0.1 or 0.5 µs and a maximum pulse width of 2 µs, or 4 µs, or 10 µs, or 20 µs, or 50 µs. These pulse trains may thus be applied to pairs of electrodes either interleaved with trains applied to other pairs of electrodes in the array, or delivered sequentially.

In a second aspect, the invention provides an apparatus for applying electrical pulses to a patient, the apparatus comprising a plurality of electrodes arranged in an array and a signal generator, the signal generator incorporating a power supply and a controller arranged to generate or supply composite stimulus pulses which make up a desired stimulus waveform. The apparatus then has a converter arranged to convert composite stimulus pulse, using a network of high speed switching elements, into sequential component pulses directed to pairs of electrodes in the array in a sequence such that successive electrode pairs are arranged to generate the respective component pulses in a cycle. The composite stimulus pulse has duration of between 4 µs and 1500 µs, or more preferably between 20 µs and 1000 µs. The component pulses have a maximum pulse width of 2 µs, or 4 µs, or 10 µs, or 20 µs, or 50 µs.

In a variation of the above, the composite stimulus pulse may be represented in the controller by a mathematical model or numerical analogue and the component pulses may be synthesized directly using a power supply and a network of high speed switching elements connected to electrodes in the array.

The component pulses may be delivered sequentially, so that at least one pair of electrodes is active at any time during the period of the composite stimulus pulse, or may have gaps of a few microseconds between them, preferably less than 20 µs, but up to a maximum of 200 µs, so that the sum of the component pulse widths is equal to the composite pulse width, but the total duration of the component pulses is equal to the composite pulse width plus the sum of the gaps between the component pulses.

In implanted stimulation apparatus, one or more electrode(s) in the array may optionally be provided by the enclosure of a stimulator device housing the signal generator and battery supply.

In a third aspect, the invention provides an apparatus for applying electrical pulses to a patient, the apparatus comprising a plurality of electrodes arranged in an array, a signal generator for generating signals to said electrodes (optionally an additional electrode provided by the signal generator enclosure), a controller arranged to control, represent or store a desired notional voltage, current, charge or energy distribution in a mathematical or empirically derived model of human or animal tissue in the region of the array, termed the "the notional stimulation field". The apparatus then has a transformation element arranged to reduce the notional stimulation field into a series of component pulses with respective duty cycles and/or amplitude so that they produce a desired notional stimulation field in a model of the flow of current between the electrodes, and a stimulator arranged to apply these component pulses to the array of electrodes. The component pulses are either sequentially transmitted to said electrodes at different times such that successive electrode pairs are arranged to generate the respective component pulses in a cycle, or alternately so that they do not all start and end at the same point in time. These component pulses are produced by one or more signal generator devices. If the number of signal generators is less than electrodes in the array, a network of high speed switching elements is provided to direct the generator outputs to pairs of electrodes in the array. The mathematical model may be complex, including the various electrical characteristics of surrounding tissues, or may be simple, such as assuming a one or two dimensional homogeneous resistive medium. An empirical model may be expressed mathematically, or as a number of reference stimulation patterns which may be interpolated between, or as a series of look-up tables or rules.

The characteristics of the notional stimulation field may be controlled by the patient, surgeon, or other operator using an operator interface that provides control of the centre and optionally the coverage area of the desired field of stimulation.

In a variation of the above, the means of calculating the desired current, charge or energy distribution in a model of human or animal tissue is provided by a computer system separate from the signal generator unit and the parameters of the desired stimulus field and/or component waveforms are transmitted to the signal generator unit.

In a fourth aspect, the invention provides an apparatus for applying electrical pulses to a patient, the apparatus comprising a plurality of electrodes arranged in an array and a signal generator for generating signals to said electrodes, the signals being short component pulses applied to pairs of electrodes such that the component pulses are generated by successive electrode pairs in a cycle, the amplitude and duration of the pulses being such that these pulses produce little or no activation of afferent fibres directly adjacent to one or more of the electrodes, but the sum of the pulses in a target region of tissue distant from one or more of the electrodes is sufficient to produce an action potential in fibres or some other physiological effect in excitable cells at this location.

This effect is arises when the combination of pulse width and amplitude of the component pulses is such that individually these pulses contain insufficient energy to activate voltage gated channels on nerve axons, but collectively the sum of the component pulses provide sufficient energy to meet the threshold level at which these channels are activated, thereby causing an action potential to be produced. The effect is particularly apparent with component pulses of duration of the order of 1 μs to 4 μs and composite pulses comprising 10 to 40 component pulses such that their duration is 10 μs to 160 μs.

In a variation of the above, the component pulses may be of a duration and amplitude that in themselves cause an action potential in the tissues directly adjacent to the electrodes, but the sum of the component pulses is also sufficient to generate additional action potentials at locations distant from the electrodes.

In a fifth aspect, the invention provides an apparatus for applying electrical pulses to a patient, the apparatus comprising a plurality of electrodes arranged in an array and a signal generator for generating signals to said electrodes, the signals being short component pulses applied to pairs of electrodes, the relative pulse widths and polarity of the component pulses being varied with respect to each other and optionally the number of electrode pairs used are also varied to change the location and the coverage area of the region of the tissues that are stimulated.

In a sixth aspect, the invention provides an apparatus for applying electrical pulses to a patient, the apparatus comprising a plurality of electrodes arranged in an array and a signal generator for generating signals to said electrodes, the signals being short component pulses applied to pairs of electrodes, the component pulse widths on any given pair of electrodes, or individual electrodes with respect to the case or ground electrode of an implanted stimulator, being determined with respect to each other to normalise the sensation on each electrode such that the perceived stimulation at the amplitude limit or same programmed amplitude on each electrode pair is the same.

The above facilitates smooth changes in the location and the coverage area of the region of the tissues that are stimulated while minimising apparent changes in stimulation intensity due to differences in the tissues or contact resistance in the region of each electrode in the array. Determination of the relative pulse widths for the component pulses may be achieved by measuring the onset of sensation or other reference level of sensation on each contact in turn with respect to the housing of the controller, or by measuring only a few electrodes and interpolating to provide an estimate for other electrodes.

Any of the first to sixth aspects discussed above may also provide a method of applying electrical pulses to a patient in which the pulses are applied via an electrode array on or in the patient.

Thus, for example, in the first aspect there may be provided a method in which signals are generated and sequentially transmitted to successive pairs of electrodes in an electrode array such that the signals are either sequentially transmitted to said successive electrode pairs in a cycle so the respective electrode pairs receive the corresponding signals at different times, or alternatively so that the signals are received by the electrode pairs such that they do not all start and end at the same point in time, thereby generating a composite pulse in the patient which has a duration between 4 μs and 1500 μs, or more preferably between 20 μs and 1000 μs, and a maximum voltage as follows:
  a) for implanted devices a maximum voltage between 2 V and 50 V, or more preferably between 5V and 20V or even more preferably between 10 V and 15 V;
  b) for transcutaneous devices a maximum voltage between 15V and 500V, or more preferably between 50V and 250V.

Similarly the second aspect may provide a method in which a composite pulse is converted into sequential component pulses which are then directed to pairs of electrodes in the array in a sequence such that successive electrode pairs are arranged to generate the respective component pulses in a cycle. The composite stimulus pulse has duration of between 4 μs and 1500 μs, or more preferably between 20 μs and 1000 μs. The component pulses have a maximum pulse width of 2 μs, or 4 μs, or 10 μs, or 20 μs, or 50 μs.

In the third aspect, a method may be provided in which a desired notional voltage, current, charge or energy distribution in a mathematical or empirically derived model of human or animal tissue in the region of the array, termed the "the notional stimulation field". The notional stimulation field is then reduced to a series of component pulses with respective duty cycles and/or amplitude so that they produce a desired notional stimulation field in the tissues or in a model of the flow of current between the electrodes, and these component pulses are then applied to the array of electrodes. The component pulses are either sequentially transmitted to said electrodes at different times such that successive electrode pairs are arranged to generate the respective component pulses in a cycle, or alternately so that they do not all start and end at the same point in time.

In the fourth aspect, a method may apply signals to a patient the signals being short component pulses applied to pairs of electrodes such that the component pulses are generated by successive electrode pairs in a cycle, the amplitude of the pulses being such that these pulses produce little or no activation of afferent fibres directly adjacent to one or more of the electrodes, but the sum of the pulses in a target region of tissue distant from one or more of the electrodes is sufficient to produce an action potential in nerve fibres or some other physiological effect in excitable cells at this location.

Similarly, in the fifth aspect, the relative pulse widths and polarity of the component pulses is varied with respect to each other and optionally the number of electrode pairs used is varied to change the location and the coverage area of the region of the tissues that are stimulated.

Equally, in the sixth aspect the maximum component pulse widths on any given pair of electrodes, or individual electrodes with respect to the case or ground electrode of an implanted stimulator is determined with respect to each other to normalise the sensation on each electrode such that the perceived stimulation at the amplitude limit on each electrode pair is the same.

In any of the above aspects, the component pulses may be varied in time relative to each other such that they are separated by a few microseconds or overlap, save that they do not all start and end at the same point in time. Variation of the spacing between the component pulses changes the level and perceived location of afferent nerve activation for a given total charge delivered. The spacing may be optimised to provide the maximum level of perceived stimulation for minimum battery drain. The spacing may be a minimum of zero and a maximum of 20 μs or 50 μs or 200 μs.

In any of the above aspects of the invention, the component pulses may be either:
  a) Individual pulses, i.e. one component pulse applied to each pair of electrodes in respect of each composite pulse.
  b) Trains of sub-component pulses, i.e. each component pulse is itself divided into trains of sub-component pulses with a space between each pulse, wherein the sum of the widths of each sub-component pulse in each train is equal to the pulse width of each equivalent component pulse, each train delivered to respective pairs of electrodes sequentially.
  c) Trains of sub-component pulses, each component pulse divided into trains and these trains of pulses interleaved with other trains of pulses applied to other respective electrode pairs, so that the first sub-component pulse from the first train is applied to the first pair of electrodes, then the second sub-component pulse from the second train is applied to the second pair of electrodes and so on until the cycle is repeated and all sub-component pulses have been delivered.

The preferred arrangements are a) and c), the choice between the two determined by the length of the composite pulse and the desired maximum duration of any component or sub-component pulse, which is typically 2 μs, or 4 μs, or 10 μs, or 20 μs, or 50 μs.

The relative duty cycle and/or amplitude of the component pulses may be determined and directed to the appropriate electrode pairs such that the desired stimulation field is produced. Additionally, each component or sub-component pulse may be modulated by shortening the pulse by a percentage of the time slice allocated to the pulse in order to provide control over the effective amplitude of the pulse.

In another aspect of the invention, an implanted stimulator apparatus comprises a stimulator device and an electrode lead which contains embedded temperature sensors, preferably platinum resistance temperature devices or thermocouples. The stimulator device is provided with precision voltage and/or current measurement which is used to measure the temperature of the electrode array and/or leads, so that heating of the simulator apparatus or adjacent tissues due to induced currents caused by diagnostic imaging scanners, electrosurgical equipment etc. may be detected and the operator or surgeon may alter or terminate the procedure before unintentional tissue damage in the region of the implanted stimulator assembly occurs. The apparatus may also provide means for monitoring electro-magnetic interference induced on the implanted leads, so that action can be taken to minimise potential heating effects, for example in a magnetic resonance imaging scanner the patient can be oriented to minimise coupling between the scanner and the implanted stimulator leads. In leads which are not provided with embedded temperature sensors, the apparatus may additionally provide monitoring of the induced electro-magnetic interference in the leads so that electrode heating effects may be estimated. Additionally, the monitoring circuit that detects electro-magnetic interference on the leads may synchronise acquisition of temperature readings with periods of low interference, such as the periods during magnetic resonance imaging when the radio frequency subsystem is not transmitting and gradient coils are static. The apparatus may also employ a two wire connection to a platinum resistance temperature device to detect changes rather than the absolute value of the electrode temperature. Note that this aspect, using embedded temperate sensors, may be used in combination with any or all of the first to sixth aspects discussed above.

The present invention addresses certain limitations or disadvantages of the prior art.

Applied to transcutaneous nerve stimulation, the relatively short duration of the component pulses immediately adjacent to each electrode allows higher currents to be applied to the skin without causing pain as a result of activating such cutaneous afferents as Aδ and C-fibres.

Radkarishnan et al 2005 demonstrated that TENS signals only produce pain relief (in, for example, an acute arthritic knee) when deeply placed fibres are stimulated. When Radkarishnan injected local anaesthetic into the deep tissues pain relief from TENS was reduced. This might explain the differing reports of TENS in man, where perhaps TENS is only effective when patients are brave enough to use it at a high enough amplitude to penetrate deep tissues, an amplitude that many would say produces an unbearable amount of tingling. Because current density is attenuated the deeper the current penetrates into tissues, the problem with TENS is how can one employ surface electrodes in a conscious person and get sufficient current density to excite axons lying in deep tissues without first having a yet higher current density in the superficial tissues—a current density often too painful to bear. The present invention offers a method of achieving high current density in deep tissues without causing painful stimulation of cutaneous afferents.

Applied to both transcutaneous and implanted stimulation, variation of the number of electrodes used in each array, the pairing of these electrodes and the component pulse width applied to each electrode allows the location and coverage area of the stimulation currents to be controlled and varied smoothly over an area of tissue covered by an electrode array. Preferably, the stimulation location and coverage area is controlled through a graphical interface and pointing device (for example a computer mouse, joystick, track ball or touch screen) which allows the surgeon or patient to control the electrode array in an intuitive manner, while the computer automatically decides the pairing and relative pulse widths etc. applied to the electrodes in the array.

The relatively short duration of the component pulses that are applied to each electrode also enables reduction in the effect of tissue capacitance, which causes the amplitude of a nerve stimulation pulse to decay in a few tens of microseconds. This droop arises with a voltage source as a droop in the current as the pulse is maintained, due to charging of capacitance in the tissues. By applying component pulses to an array of electrodes, the tissue capacitance in the tissue local to the electrodes is charged only by the individual component pulses. Potentially therefore, the invention allows the current flowing in deep tissues to be increased as compared with a device producing a single broad pulse.

Another advantage of the present invention is that the design of stimulators with many outputs may be simplified; this applies in particular to implanted stimulators. In the prior art, stimulators with multiple outputs are provided with an independent voltage or current source for each output, or alternatively with fewer voltage or current sources than the number of outputs, and a relatively low bandwidth means of multiplexing these sources to the outputs. In the former case, independent control of each output provides flexibility over the mapping of the notional stimulation field which may be provided by combining any number of available electrodes to produce the desired stimulation. However, the complexity of providing multiple outputs (typically sixteen or seventeen) is such that the voltage or current sources are typically constructed using analogue electronics in order to minimise space requirements, to satisfy the present trend towards smaller implants for ease of implantation. Analogue methods have the advantage that they can be implemented on chip and are therefore compact, but they have the disadvantage that they are inefficient, which wastes battery power. In the case where a few voltage or current sources are multiplexed onto many outputs, the few voltage or current sources may be constructed using switching electronics, such as switch-mode power supplies. This is efficient but bulky because external inductors or capacitors are required for each supply. This method has the disadvantage that the number of electrodes that can be controlled independently is limited by the number of current or voltage sources available.

In its simplest physical realization, the invention may require only a single current, voltage, charge or energy source to produce the desired composite pulse, which is then fed to a high speed switching network that breaks up the composite pulse into the component pulses that are applied to each electrode pair. The paths of the component pulses intersect in the tissues to reconstruct the composite pulse. The advantage of this method is that a single, efficient switching supply can be used, while providing independent control of the current or voltage applied to each electrode in the array. Such an apparatus may be made more efficient than the analogue current sources described in the prior art, thereby increasing battery life, which is particularly important in implanted devices. Such an arrangement also has the advantage of being very compact, as the single switching supply can be designed to operate directly from the power source or battery.

Ideally the bandwidth of the switching supply should be high enough to allow the amplitude of the component pulses to be controlled over the period of each pulse, which may be of the order of one microsecond. A high bandwidth current source, with minimal energy storage on the output side, or a means of either dissipating or regenerating into the battery excess energy stored on the output of the supply is desirable, but difficult to realise in practice due to the very high switching frequency required.

A simpler option is a fixed voltage supply, for instance fixed at the desired maximum output voltage of typically 15V in an implanted device, where the average voltage on each component pulse is varied by modulation of the percentage of the time slice (i.e. the pulse width) allocated to each component pulse as a percentage of the total time available to each component pulse by control of the switching times on the switching network. Feedback of current flowing during the application of the component pulse may be used to control this modulation, thereby controlling average current delivered during the pulse.

An improvement on the above is to provide a variable voltage supply, with relatively low bandwidth and consequently relatively low switching frequency, such that the voltage is essentially fixed during the period of the component pulse. The effective amplitude of each component pulse is then adjusted by modulating the component pulse width as described above, either to achieve a desired average current level, voltage or charge per pulse.

A further variation is to employ a variable amplitude power supply, for example a voltage supply, and a sensor or sensors that measure the current and/or voltage for each component or sub-component pulse (either by averaging these throughout a pulse or by sampling them one or more times), then feed back this data to modify the relative duty cycles of the component pulses so as to achieve the desired average current, voltage, charge or energy distribution among the respective electrode pairs and to modify the overall amplitude of the power supply to achieve the desired average current, voltage, charge or energy in the composite pulse as a whole. The feedback loop may be implemented in the conventional way by applying correction to the respective duty cycles in real time, or on a cycle-by-cycle basis by applying corrections to the next cycle on the basis of data from the previous cycle. The cycle-by-cycle method has the advantage that the corrections may be calculated using a relatively low performance microprocessor in the time between each cycle, whereas the real time method requires either analogue feedback or fast digital processors. The cycle-by-cycle feedback method is unable to compensate for variation in load impedance that occurs over the period of the stimulus pulse, but in practice impedance varies only relatively slowly so this is not a significant disadvantage.

A combination of the above schemes described in the preceding two paragraphs may be appropriate, particularly in the case where the apparatus has a power supply whose amplitude is variable within a restricted dynamic range. For example, in a voltage supply it may be convenient to vary the output voltage between the battery supply and the maximum output, but not down to zero voltage. If amplitude below the battery voltage is required, the component or sub-component pulses are pulse width modulated to reduce the effective amplitude of the applied pulses.

Another option is to provide a variable voltage power supply based on switching techniques, supplying an analogue current source which in turn feeds a switching matrix which directly synthesizes the component or sub-component pulses by connecting the appropriate electrode pairs in turn as required. The advantage of this approach is that the variable voltage source may be electrically efficient, providing only enough headroom voltage for the analogue current source to have good control. The combination of a switch mode variable voltage supply with analogue current source is a good compromise between electrical efficiency and electronic complexity, while providing the high bandwidth and low noise that an analogue output stage may provide.

Other options include a fixed current supply with pulse width modulation of the switching matrix, or other combination of fixed or variable voltage, current, energy or charge control.

DETAILED DESCRIPTION OF THE INVENTION

The invention can be illustrated by considering examples of its application to transcutaneous and implanted stimulators. The figures illustrating electrode arrays may be considered to be representative either of a clinical situation or of a corresponding mathematical model of the tissues used to derive the appropriate component waveforms. The pulses in the figures can be considered to be representative of current, voltage, charge or energy, depending on the method of control used by the stimulator device.

Figure 1:
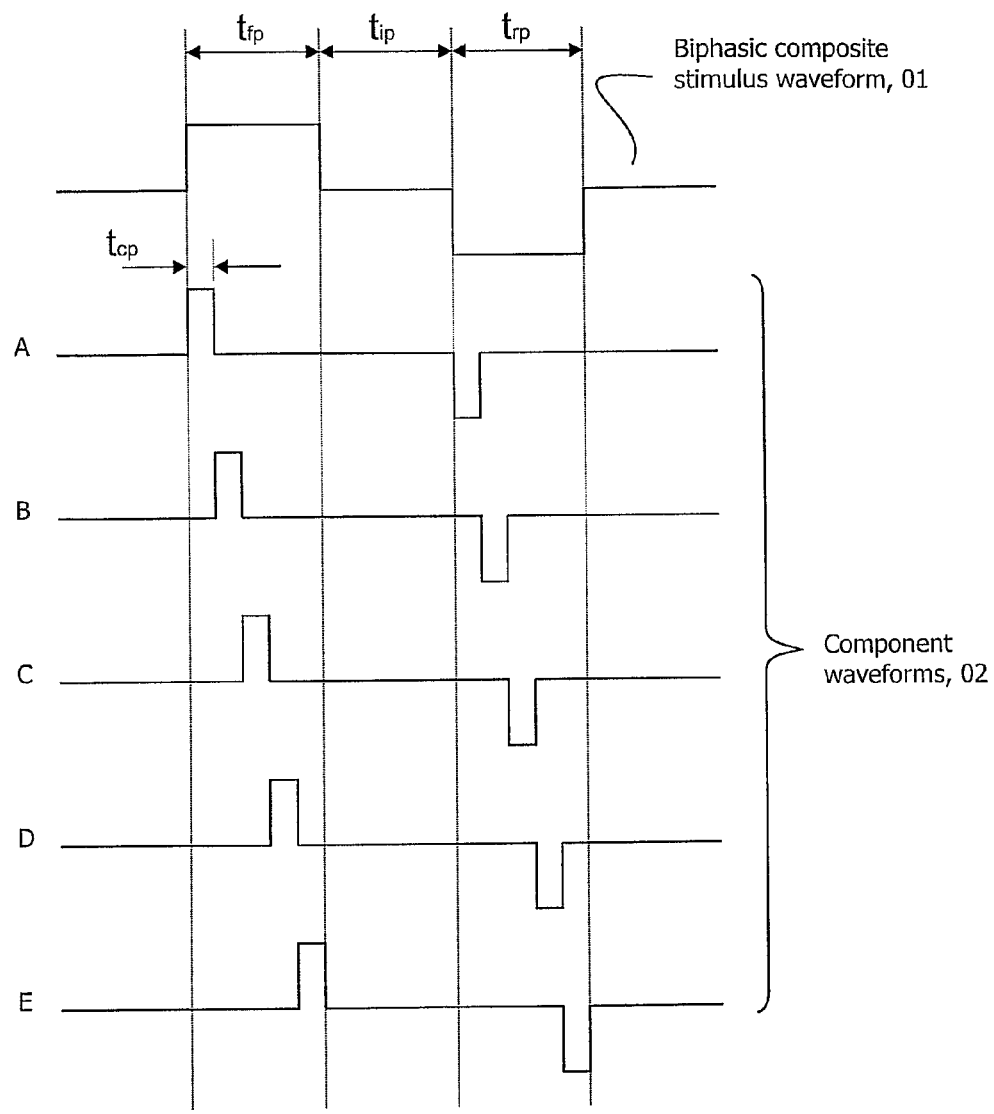
FIG. 1 shows an example of a typical bi-phasic square wave TENS waveform and the component waveforms A to E that are applied to each of the electrodes A to E in the linear array illustrated in FIG. 2.

Referring to FIG. 1, waveform 01 is a composite waveform required to affect the behaviour of excitable tissue in, for example, a transcutaneous nerve stimulation application. The waveform in this example consists of balanced forward and reverse composite pulses, the forward pulse of duration $t_{fp}$ (which may typically be 50, 100, 500 or 1000 μs) and the reverse pulse of duration $t_{rp}$, with $t_{fp}=t_{rp}$, so that the net current flowing in the tissues is zero. Net zero current flow is preferable because it minimises ionic transport between the electrodes which can cause skin reactions. The forward and reverse pulses may be separated by an interpulse spacing $t_{ip}$, which may be zero. The composite waveform, 01, is broken into five component waveforms, labelled A to E. In this example, the resistance between any two pairs of electrodes is assumed to be equal and the desired amplitude of each component pulse of the component waveform is equal, consequently each component pulse is of equal duration. Each component waveform consists of a forward pulse of $t_{cp}$ μs duration, where $t_{cp}=t_{fp}/5$, followed $t_{fp}+t_{ip}$ μs later (measured between leading edges) by a reverse pulse of $t_{cp}$ μs duration. Each component waveform is identical except that it is delayed in time by $t_{cp}$ μs from the start of the previous component waveform. Adding component waveforms A through E together produces the original composite waveform, 01.

Figure 2:
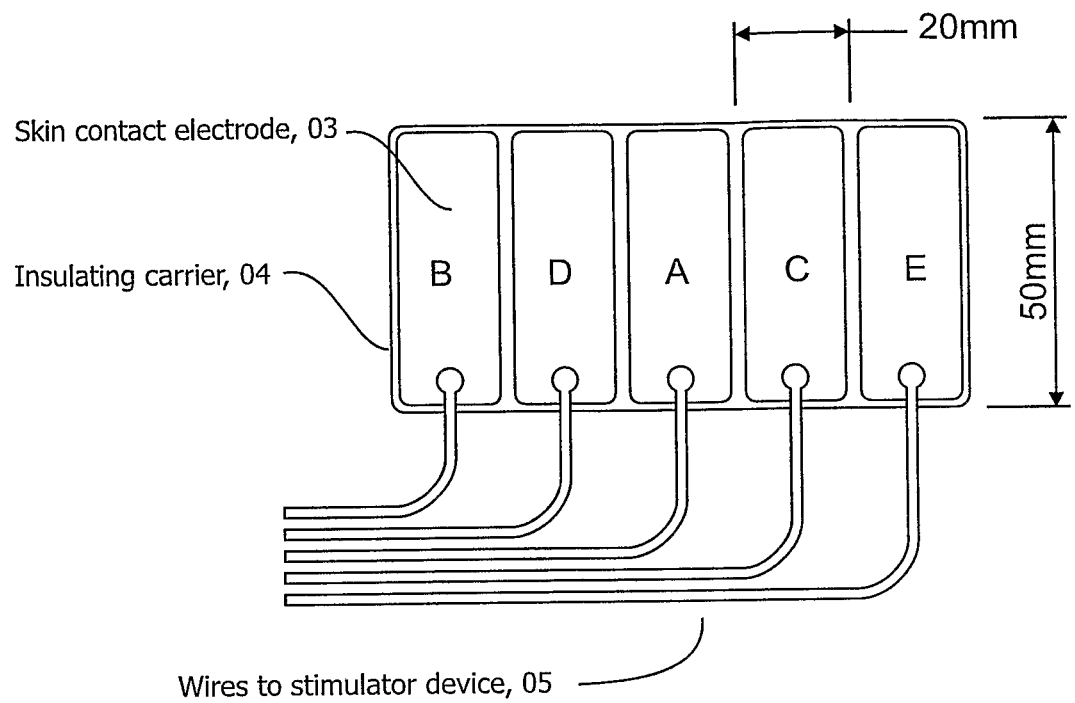
FIG. 2 shows a transcutaneous electrode array with five electrodes labelled A to E arranged in a linear array.

FIG. 2 shows a linear electrode array consisting of five electrodes, 03, mounted in this example at 20 mm pitch on an insulating backing sheet, 04. Each electrode in the array is labelled A to E, corresponding to the component waveforms in FIG. 1.

Figure 3:
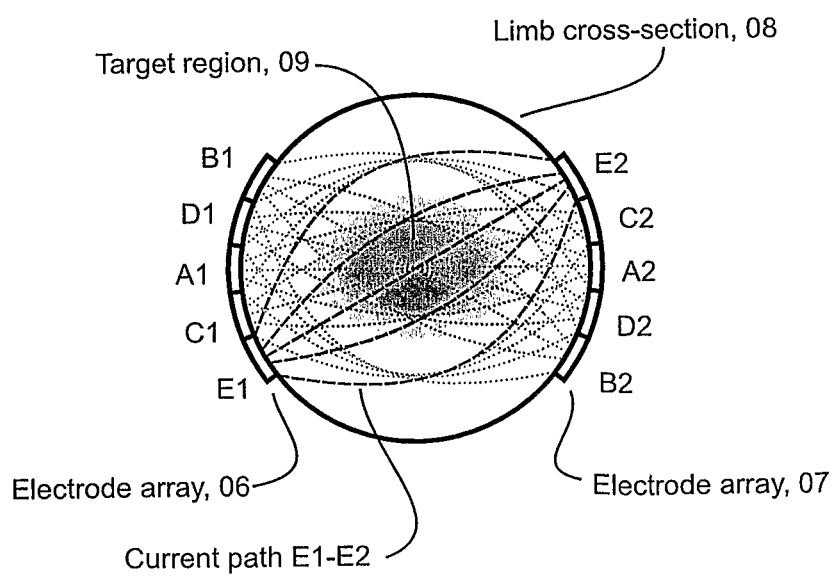
FIG. 3 shows the current paths in tissues through a cross section of a notional homogenous limb wherein two linear electrode arrays according to FIG. 2 are applied transcutaneously on either side of the limb.

FIG. 3 shows an example application of two linear electrode arrays labelled 06 and 07 of the type shown in FIG. 2. Each of the electrode arrays is positioned either side of a limb, 08, such that the component waveforms, A to E, are applied across electrode pairs A1-A2 etc. The respective current path through the tissues for each of the electrode pairs is illustrated approximately by the dotted lines shown, such as current path E1-E2, shown in bold.

It can be seen that the current paths of the component waveforms cross in the tissues in the area demarked by the shading. Afferent nerves or other excitable tissues in the shaded region will tend to be affected by a composite waveform similar in duration to the composite waveform, 01, in FIG. 1, whereas the afferent nerves or other excitable tissues in regions outside this shaded region will tend to be affected by the by individual component waveforms (02 in FIG. 1) for a correspondingly shorter duration.

The diagram is of course an idealised case assuming that the limb is homogeneous in cross-section; in a clinical situation the current will follow a path dictated by the relative conductivity of different tissues and bone etc. In both cases, the current path spreads out as it transits between the two electrode pairs, with its start and end point defined by the arrangement of the electrode pairs. A crossing arrangement as shown provides a point of focus for the stimulating waveform in the deep tissues, whereas an alternative non-crossing arrangement (where each electrode pair is opposite each other analogous to rungs on a ladder) provides a more distributed region of stimulation. It is also possible to vary the shape of the region of stimulation and the centre of this region by varying the relative duty cycle of the component waveforms and the pairing of electrodes.

Figure 4:
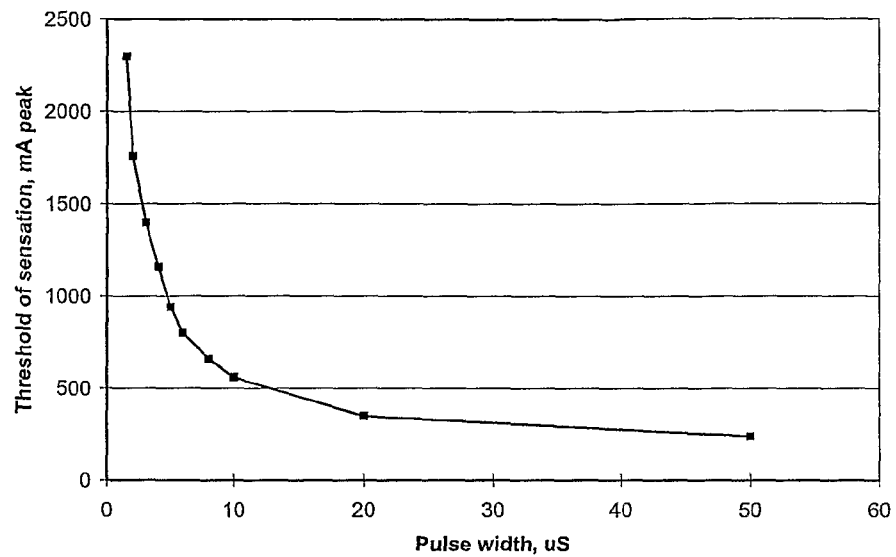
FIG. 4 shows the relationship between peak pulse current at first onset of sensation and pulse width for a square wave pulse repeated at 100 Hz applied transcutaneously via two square 50 mm×50 mm electrodes placed mid forearm one on the anterior and the other on the posterior surface.

The effect of pulse width on sensory threshold is illustrated by the graph in FIG. 4. This graph shows the variation of peak pulse current with pulse width at the threshold of sensation. The pulse current was recorded between one pair of electrodes at the amplitude at which a test subject detects initial onset of sensation. The pulse was a square wave voltage pulse repeated at 100 Hz applied transcutaneously using two square 50 mm×50 mm electrodes, placed mid forearm one on the anterior and the other on the posterior surface. This example is for one subject, an adult male. It will be appreciated that the current will vary with subject and with the type and placement of the electrodes. In particular, implanted electrodes require much less current to cause sensation because of the lack of skin resistance and the typical smaller size of the contact area, thereby providing higher current density at the electrode. Nevertheless, the general shape of the curve remains the same, an approximately exponential decline in stimulus current as pulse width is increased.

For transcutaneous application, selection of appropriate component pulse widths and stimulation intensity, together with placement of the array electrodes so that the currents in deep tissues tend to add, can generate action potentials in the deep tissues without activating the cutaneous afferents.

However, it is possible to activate the cutaneous afferents by a train of short pulses which individually do not have sufficient energy to generate an action potential, as they are individually of insufficient energy to activate voltage gated channels on the nerve, but they may do so by summation. Because of the close proximity of the electrode segments in the array, it may therefore be that the pulses from adjacent segments will add together. In the design of a transcutaneous stimulator which has the object of minimal activation of cutaneous afferents, the electrodes in FIG. 3 are activated in a sequence that ensures that no two adjacent segments are activated in turn. The labelling of the component waveforms in FIG. 1 and their corresponding electrodes in FIGS. 2 and 3 is an example of such a sequence. It is also preferable that each segment in the array shown in FIG. 2 is separated by a few mm.

In this example, tissues directly beneath the electrode segments are subject to a pulse width that is no more than one fifth of the composite pulse duration. At particular stimulation intensity this may be insufficient to activate the cutaneous afferents. However, in deeper tissues, the applied signals tend to flow through the same tissues. The individual short pulses will add together in turn to reconstruct the longer pulse of the form of composite waveform, 01, in FIG. 1. This leads to an interesting effect whereby it is possible to stimulate a nerve innervating a region distant from the site of placement of the electrodes, without directly stimulating the tissues directly under the electrode arrays.

Furthermore, in a system that includes balanced forward and reverse pulses as illustrated in FIG. 1, the spacing between the forward and reverse pulses (of a given amplitude and duration) affects stimulation intensity. Perceived stimulation intensity increases as the spacing increases from zero to about 20 µs, stays relatively constant to about 200 µs and decreases as the spacing is increased further still. This effect is most apparent for pulses of a few microseconds duration, such as typical component pulse durations of 1 to 20 µs. In a system which has zero net current flow, but requires minimal activation of cutaneous fibres, it is preferable therefore that the reverse pulse is separated from the forward pulse in time, or alternately occurs immediately after the forward pulse. The latter is difficult to achieve because the reverse component pulse in must be separated from the forward pulse by at least the duration of the composite pulse (measured between leading edges). Consequently, in a typical system where the composite pulse repetition rate is 100 Hz, the spacing may preferably be such that the balancing reverse pulses occur half way between the forward pulses, i.e. 5,000 µs after the leading edge of the forward pulse. An alternative approach is to provide the balancing reverse charge by means of a gradual reverse charge in between forward pulses. Because of the low mark-space ratio of a typical nerve stimulation waveform, this balancing reverse charge can be arranged to occur at an amplitude that is well below the level at which afferent fibres are activated.

In one application of the five electrode array described, two electrode arrays are placed directly over a painful region, for example an injured knee, and the stimulation intensity is increased until the patient determines it is at the maximum comfortable level. At the maximum comfortable level with a five electrode array, both cutaneous and deep afferents are typically firing. A comparison between the array device described herein and a standard TENS device with electrodes of equivalent area shows that users could not easily differentiate between sensations generated by cutaneous and deep afferents. Some subjects describe the array device to be "more penetrating", but the difference in sensation between the two devices is not marked. However, at equivalent maximum comfortable levels, the current flowing in the tissues from the array device is typically three times that of the standard TENS device. An advantage of this method is therefore that the pain threshold when measured in terms of current applied is increased—in this example three-fold.

Figure 5:
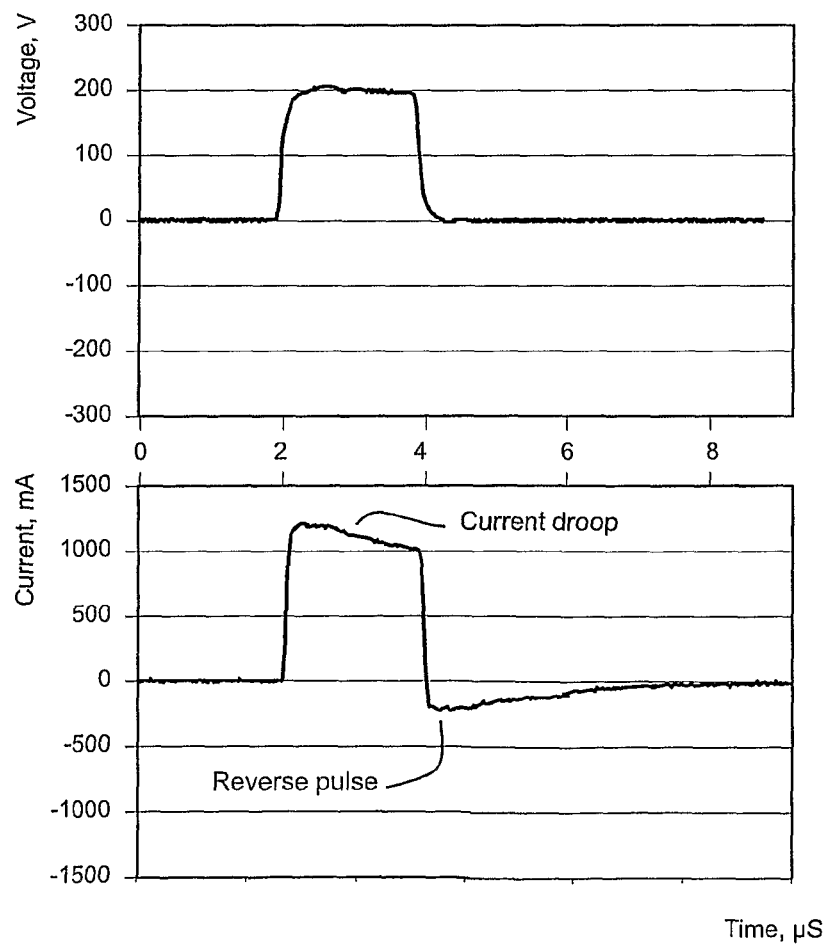
FIG. 5 shows a voltage pulse applied transcutaneously, showing current droop during the pulse.

Another advantage of the method is that capacitive effects in the tissues are reduced. These effects are illustrated in FIG. 5 for a short pulse of 2 µs. Because of the capacitance of tissues, a square voltage pulse produces a current that droops during the pulse and on removal of the voltage produces a return current pulse. As the pulse width is extended to typical composite pulse lengths of 50 to 100 µs, this effect produces a marked reduction in charge delivered during the pulse. Because the component pulses are shorter than the composite pulse, current in deeper tissues can be maintained at a higher level than a traditionally derived broad duration pulse such as that produced by a TENS device in the prior art.

Figure 6:
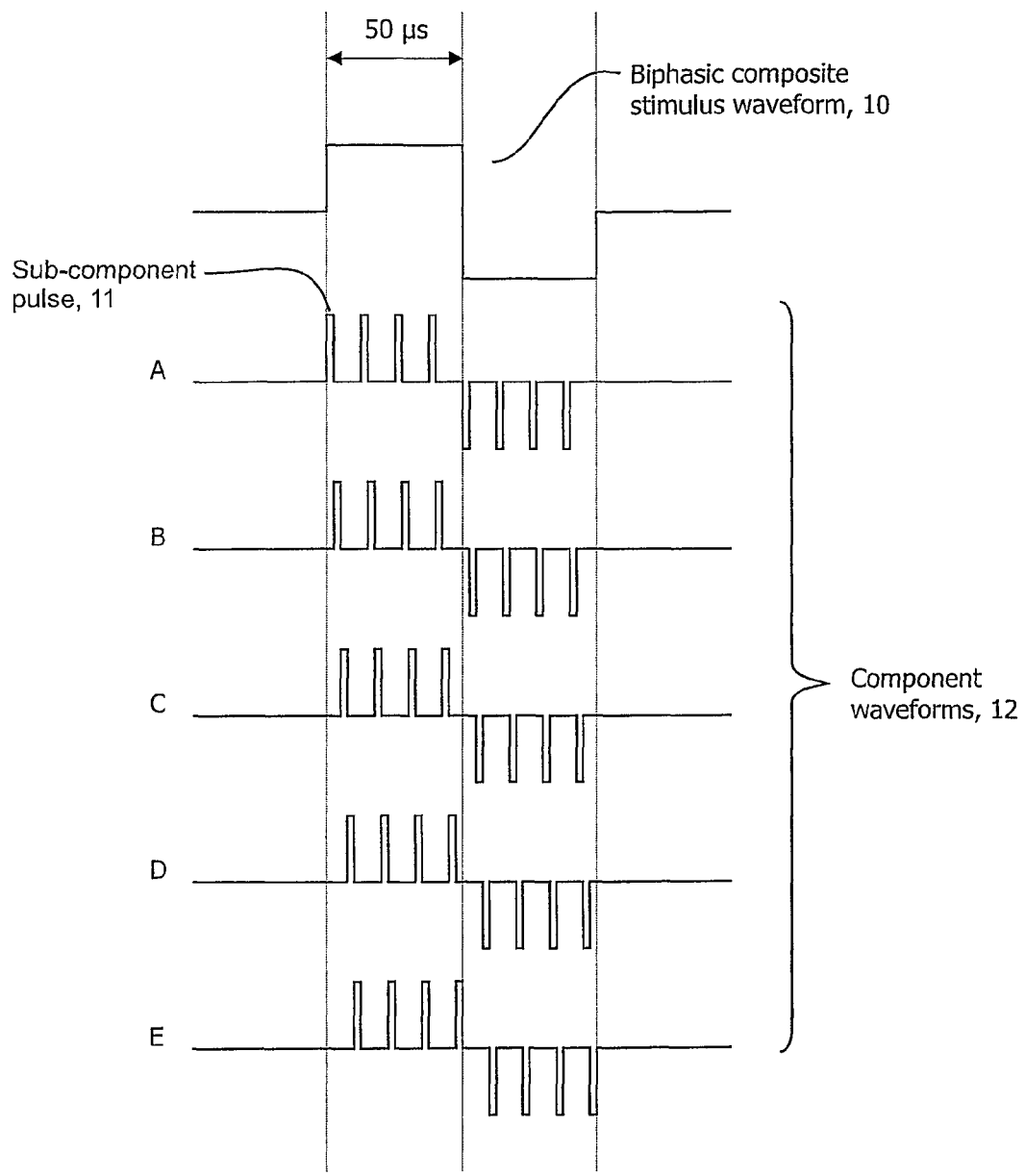
FIG. 6 shows an example of a typical bi-phasic square wave pulse of 50 μs duration and component waveforms A to E that consist of pulse trains of 2 μs component pulses.

A further benefit in this regard is obtained by breaking the component pulses into in trains of sub-component pulses. This is illustrated in FIG. 6, wherein a desired composite waveform, 10, with equal forward and reverse pulses of 50 µs duration with zero inter-pulse spacing is broken into five component waveforms, 12, A to E, each consisting of a train of 2 µs sub-component pulses, 11, repeated at 10 µs. Even though most figures in this text show the basic (i.e. single pulse) component waveforms for clarity, the higher frequency pulse train form is the preferred method for long composite pulse durations where the component pulses might exceed a desired maximum duration. In the preferred embodiment, the sub-component pulse trains are derived so that the minimum pulse width of any sub-component pulse is 0.1 to 0.5 µs and the maximum is between 2 and 20 µs.

The pulse train waveform might be expected to further reduce activation of cutaneous afferents in favour of deep afferents. This is indeed the case, but in practice this effect is not as marked as would be expected from inspection of the graph in FIG. 4 because of the aforementioned summation process that results in generation of an action potential from a series of very short pulses that might not themselves normally be expected to cause activation. However, the method does allow higher current to be applied to the skin without discomfort around the electrodes.

With a transcutaneous arrangement described above, there is an inevitable compromise between the number of electrodes in the array, the complexity of the stimulator device and weight of the cable that connects each electrode array to the stimulator. One means of overcoming cabling weight is to construct a switching matrix on a flexible substrate on the back of the electrode array. This can operate using a two wire supply from the stimulator and multiplex the signal to the array on the basis either of time from start of the composite pulse, or using a three wire supply with a separate clock signal from the stimulator.

Figure 7:
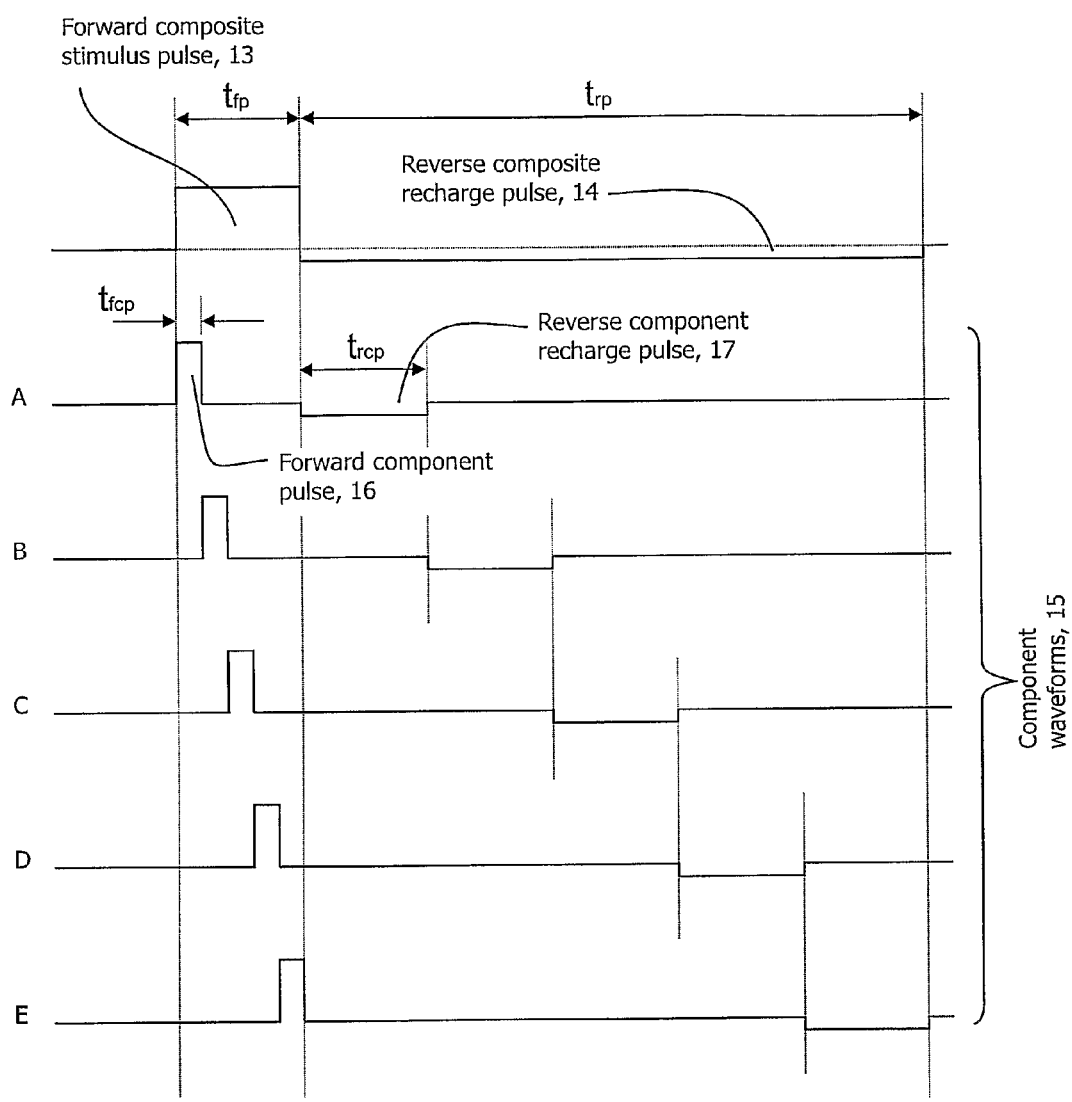
FIG. 7 shows an example of a forward square wave composite pulse with a synthesized low amplitude recharge pulse and the resulting component waveforms.

In previous examples, the composite pulse consists of balancing forward and reverse pulses of the same amplitude and duration. Although not an essential feature of this invention, it is preferable that the sum of forward and reverse charges is zero to prevent ionic transport between electrodes, although the shapes of the forward and reverse pulses do not have to be the same. FIG. 7 illustrates such an example, in this case the forward pulse, 13, is the same as shown in FIG. 1, but zero net charge is provided by a gradual reverse recharge, 14, between forward pulses. Typically, the forward pulse accounts for 1% or less of the total cycle duration, so the reverse recharge can occur during the relatively long quiet period between forward pulses at well below the amplitude which activates nerves.

The reverse recharge pulse can be achieved by simply generating the desired forward pulse with a suitable signal generator, and coupling this to the tissues via a series capacitor, although the recharge should preferably be controlled so that it does not interfere with other component pulses, which introduces additional complexity.

Alternately and preferably, the reverse pulse can be generated explicitly by a signal generator with bipolar output, or a mono-polar signal generator with a suitable switching matrix on the output. FIG. 7 illustrates an idealised current waveform in such a system, the desired composite stimulus pulse, 13, is balanced by a reverse recharge pulse with the same area under the curve, 14. The forward stimulus pulse would normally be negative going (i.e. the cathode). For clarity, the positive return recharge pulse shown in the drawing has five times the duration of the forward pulse and one fifth of the amplitude. However, in a practical implementation the return pulse would only be a single digit percentage of the amplitude of the forward pulse and consequently of longer duration, sometimes occupying most of the quiet period between forward pulses. Preferably, in apparatus without a series capacitor on the output, the output stage includes a circuit that integrates forward and reverse current flow on each electrode as a cross check that the net current flow is maintained at zero. The error from this integrator is fed back into the system to modify the duration of the return pulse on each channel.

Each forward component pulse, 16, is derived as described previously, based on the desired stimulus field (in this example all component pulses are of equal magnitude but this should not be construed as limiting). The reverse component recharge pulse, 17, is calculated to have the same net charge as the forward component pulse and delivered in turn as illustrated. The component waveforms, 15, may be delivered to the electrode array as previously described in FIGS. 2 and 3, or if desired the anode may be comprised of one larger electrode, with the active array just at the cathode (i.e. that delivering the negative going forward component pulses). This provides for a simplification of the electrode array and output electronics in the stimulator apparatus.

Figure 8:
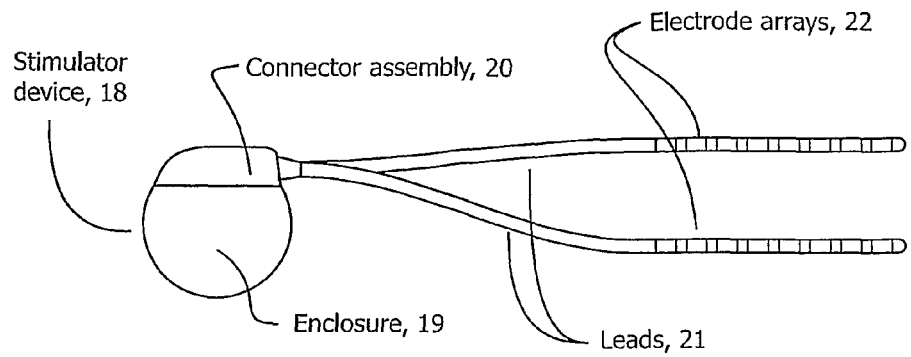
FIG. 8 shows an implanted stimulator and electrode assembly.

FIG. 8 illustrates a typical configuration of an implanted stimulator. The implanted stimulator comprises the stimulator device, 18, which contains the electronics, battery, charging electronics and signal generator(s) contained within an enclosure, 19, which is typically a hermetically sealed titanium shell. On top of the device, a connector assembly provides connection to one or more leads, 21, (shown shortened in the drawing) which terminate in one or more electrode arrays, 22. The enclosure, 19, if made of conductive material may also be used as an electrode and optionally may form part of the available array of electrodes. A typical modern implanted stimulator will have provision for a number of electrode contacts, typically sixteen arranged as two sets of eight outputs. Applications of implanted stimulators include spinal cord stimulation, where the electrodes are implanted in the epidural space, and deep brain stimulation, where electrodes are implanted in the brain.

Figure 9A:
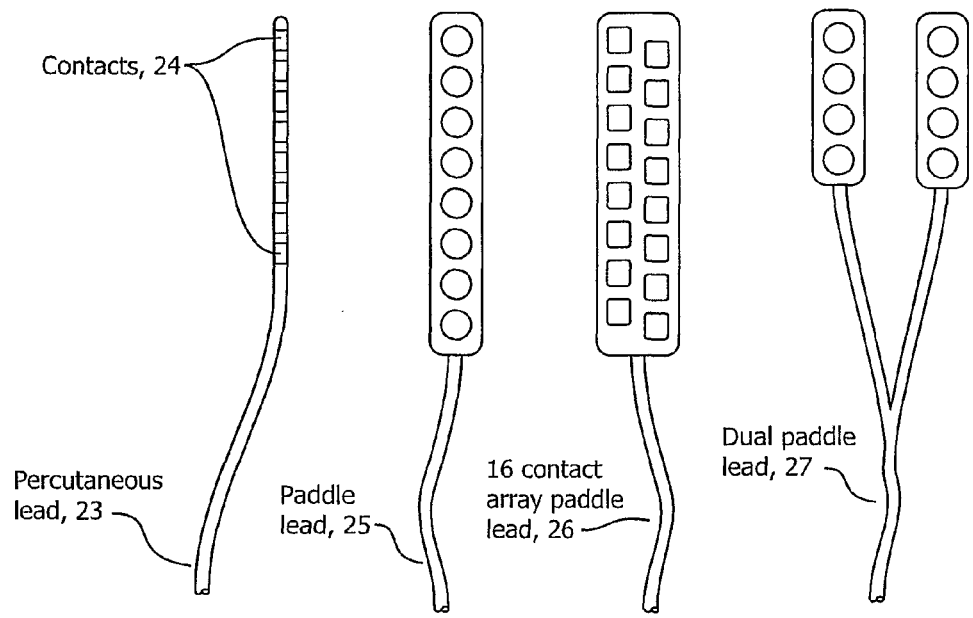
FIG. 9*a* gives examples of typical implanted electrode lead configurations in the prior art, showing common electrode configurations at the distal end.

Examples of known implanted lead types for spinal cord stimulation are shown in FIG. 9a, each comprising a number of electrode contacts in an array. Lead types include the percutaneous lead, 23, which has a number of contacts in line, 24, spaced regularly or irregularly on a flexible lead. The percutaneous lead is so named because of its ease of implantation using a hollow needle introducer as a guide. Other types of lead include the paddle lead, 25, so named after its shape. This type of lead is more invasive to implant, but has the advantage that it is less prone to migration once implanted. Many different types of paddle leads exist, including types with a multiplicity of electrodes arranged in a predefined array, 26, and types with two or more individual paddles connected to a common lead, 27. In each case, the individual contacts have respective small diameter wires embedded in an insulating sleeve that provides electrical connection to a stimulator device. One, two or more leads may be installed to cover a particular tissue or nerve area. To facilitate use of hollow needle introducers for percutaneous leads (FIGS. 9a, 23), the diameter of the connector to the stimulator device should ideally be the same as the lead.

Figure 9B:
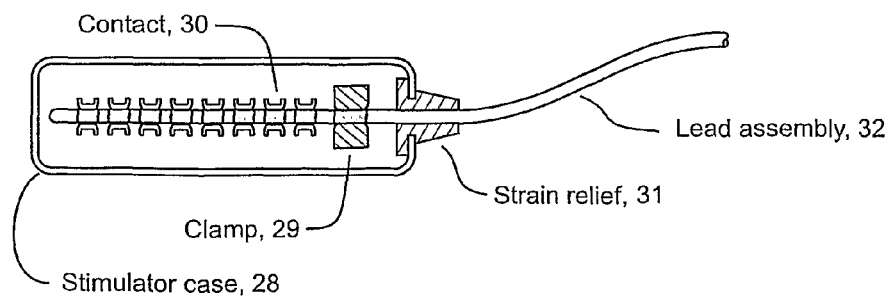
FIG. 9*b* is a top sectional view of a typical stimulator connector arrangement with the lead inserted into the stimulator device.

A typical stimulator connector arrangement is illustrated in FIG. 9b. The drawing shows the lead, 32, inserted into the stimulator device. A strain relief, 31, is provided to reduce flexing of the lead at the exit point from the stimulator. A series of spring loaded contacts, 30, provide electrical connection between the electrodes and the stimulator outputs. A clamp, 29, is adjusted by a set-screw to secure the lead. The clamp may be used as an additional contact if required.

Whatever the target tissue area, implantation is an inexact science and therefore a multiplicity of contacts allows the neurosurgeon to span a particular area of tissue and experiment with different combinations of electrodes in the array to produce a desired therapeutic effect. Migration of the lead over time or changes in the contact impedance due to the accumulation of scar tissue around the implanted electrodes may necessitate reprogramming of the electrode combination over time. Furthermore, the electrode spacing may be physically large when compared with the area of tissue to be stimulated, so a means of controlling excitation that provides variation of the point of stimulation to a finer resolution than the electrode pitch is preferred. The surgeon (or patient) should have control of a number of parameters in order to optimise the stimulation pattern, these include the amplitude of the applied stimulation (absolute current, voltage, charge, energy or a normalised value of these based on contact impedance or perceived sensation), the pulse width of the composite pulse, the repetition frequency of the pulse, the location of the centre of the area of stimulation and whether the stimulation pattern is tightly focused around the centre, or distributed more widely in the tissues.

In order to control the position of the centre of stimulation according to this invention, a composite waveform is separated into two or more component waveforms. The duty cycle of the pulses of the component waveforms and the number of electrodes recruited are controlled so that the component waveforms recombine in the tissues to reconstruct composite pulses forming the composite waveform in the desired location over a desired coverage area.

Figure 10A:
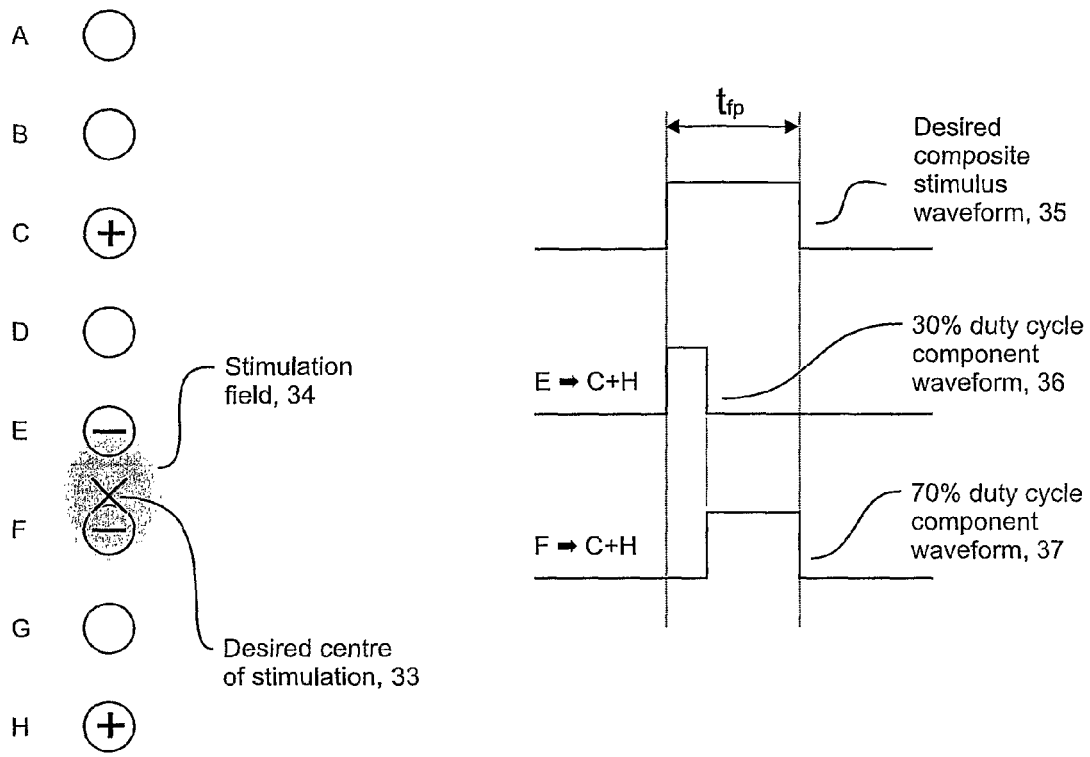
FIG. 10*a* shows an example of a focused stimulation field produced by a composite pulse using two cathodes and two anodes in a linear array and the basic component waveforms (the low amplitude recharge pulse or return pulse is omitted for clarity).

The simplest example is a linear array, such as a percutaneous or paddle lead (FIGS. 9a, 23 and 25). FIG. 10a shows a linear array of eight contacts labelled A to H, each represented by a circle in the figure, together with the basic component waveforms with the aforementioned low amplitude recharge pulse or return pulse not shown for clarity.

With such an array, it is desirable that the centre of the area of stimulation is controllable seamlessly from top to bottom of the array. In FIG. 10a, the centre point is at approximately $^{3}/_{10}$ths of the distance from electrode F to electrode E, indicated by the cross, 33 which shows the desired centre of stimulation. In practice, the stimulation is perceived over a diffuse area (the "stimulation field") indicated by the shading, 34. In most cases the cathode is preferred electrode for nerve stimulation (although it should be noted that sensation can occur at both cathode and anode). This example uses a waveform of the type illustrated in FIG. 7, consisting of a forward pulse delivered at the cathode (indicated by the minus signs over electrodes E and F in FIG. 10a), with a low amplitude reverse charge which is not shown but would be similar to that illustrated in FIG. 7.

The anodes in FIG. 10a are electrodes H and C in the array, marked with a plus sign. The desired composite stimulus waveform is a square wave pulse, 35. In order to derive component waveforms, 36 and 37, some assumption about the electrical characteristics of the tissues must be made. In the simplest case we could, for example, reasonably assume that the perceived point of stimulation is proportional to the duty cycle of the two cathodes, E and F. Hence, the component waveforms, 36 and 37 respectively in FIG. 10a are active for 30% and 70% of the forward stimulus pulse time, $t_{fp}$.

Figure 10B:
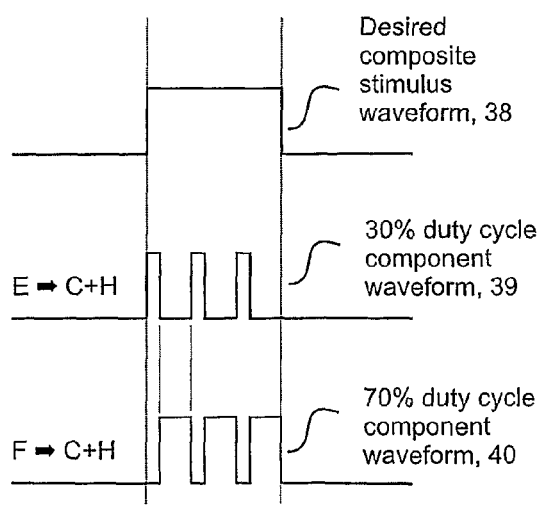
FIG. 10*b* shows an alternative arrangement of the component pulses associated with the example in FIG. 10*a* comprising high frequency component waveforms, consisting of trains of sub-component pulses.

FIG. 10b illustrates a refinement whereby the component waveforms, 39 and 40, are further subdivided into higher frequency pulse trains with the same 30% and 70% duty cycles. As previously discussed, with long composite pulses, this is the preferred method of applying component pulses as it tends to reduce the effects of tissue capacitance and ensures that the nerves in the region of electrodes E and F perceive the two component waveforms as one. In this example, the component waveform, 39 is applied to cathode E with both anodes C and H active, and component waveform, 40 is applied to cathode F also with anodes C and H. The choice of anode(s) has an influence on the current path and the current density in the region of the array; in some instances it may be appropriate to use the enclosure of the stimulator as the anode, or only one other electrode in the array to provide a more tightly controlled current path.

Using this arrangement, the centre of the stimulation field, 33, may be varied smoothly up and down the array, by controlling the relative duty cycle applied to each electrode. Furthermore, by recruiting additional cathodes, D and G, and sharing the duty cycle between four electrodes, it is possible to provide a more diffuse stimulation field, covering a wider area. It is also possible to extend this method to cover multiple electrodes implanted in a line.

Figure 10C:
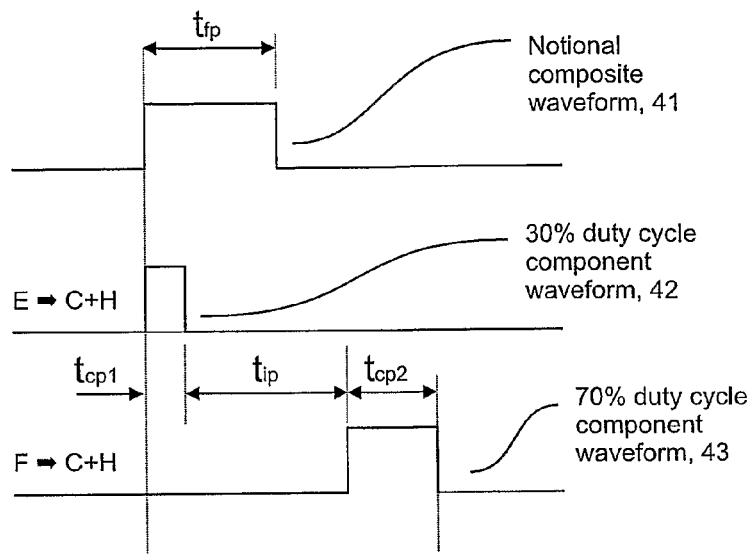
FIG. 10*c* shows an alternative arrangement of above comprising component waveforms with extended inter-pulse spacing.

FIG. 10c illustrates a further variation in the component waveforms wherein delivery of component pulses is delayed by an inter-pulse period $t_{ip}$. As before, the sum of the component pulse widths, 42 and 43, $(t_{cp1}+t_{cp2})$ is equal to the total length of the forward composite pulse, $t_{fp}$, 41, and the relative duty cycle is identical. The effect of the interpulse spacing, $t_{ip}$, is to increase the level of nerve activation for a given composite pulse duration and amplitude. The effect increases up to $t_{ip} \approx 20$ µs and is useful as it increases the battery life of the stimulator at a particular level of perceived sensation.

Figure 10D:
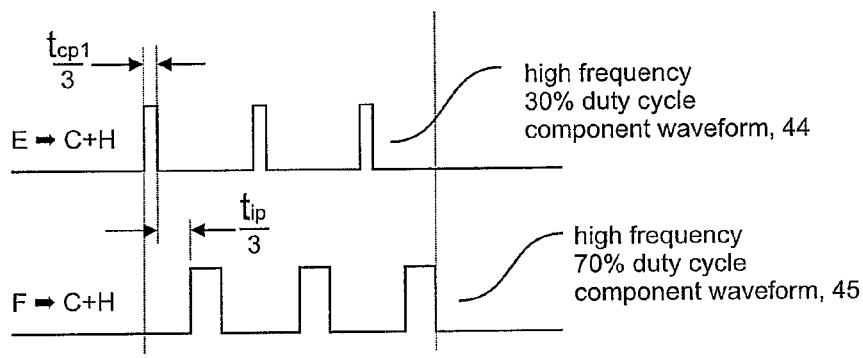
FIG. 10*d* shows an alternative arrangement of above comprising high frequency component waveforms with extended inter-pulse spacing.

The method is also applicable to the high-frequency case wherein each component pulse is broken up into pulse trains as previously discussed, and is particularly advantageous if the pulse width of the resulting sub-component pulses are in the range 1 µs to 5 µs, because the effect of increasing inter-pulse spacing is maximized within this range. This is illustrated in FIG. 10d, wherein the high frequency component waveforms, 44 and 45, each have a pulse width of one third of the length of those illustrated in FIG. 10c, and the interpulse spacing is reduce to $t_{ip}/3$ thereby completing the cycle in the same overall time.

Figure 10E:
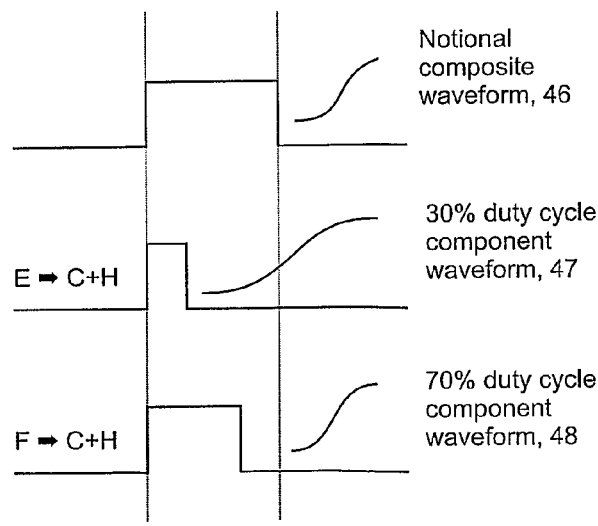
FIG. 10*e* shows an alternative arrangement of above comprising overlapping component waveforms.

FIG. 10e illustrates a further variation in the application of component waveforms. In this example the notional composite stimulus waveform, 46, is the same as previously and the component waveforms, 47 and 48 are of the same duration and amplitude, but rather than be delivered in sequence they start at the same point in time, but end at different times.

Another variation is to fix the duty cycle, but vary the amplitude of the pulses to provide the desired sharing of the charge or energy of the composite pulse between the respective electrodes. This method has the disadvantage that it requires either multiple supplies, or one very high bandwidth supply.

FIG. 10a-10e and FIG. 11 below do not show the reverse pulse for clarity, but such a reverse pulse, either a low amplitude pulse similar to that illustrated in FIG. 7, or a balancing reverse pulse similar to that illustrated in FIG. 1 would typically form part of the waveform.

Figure 11:
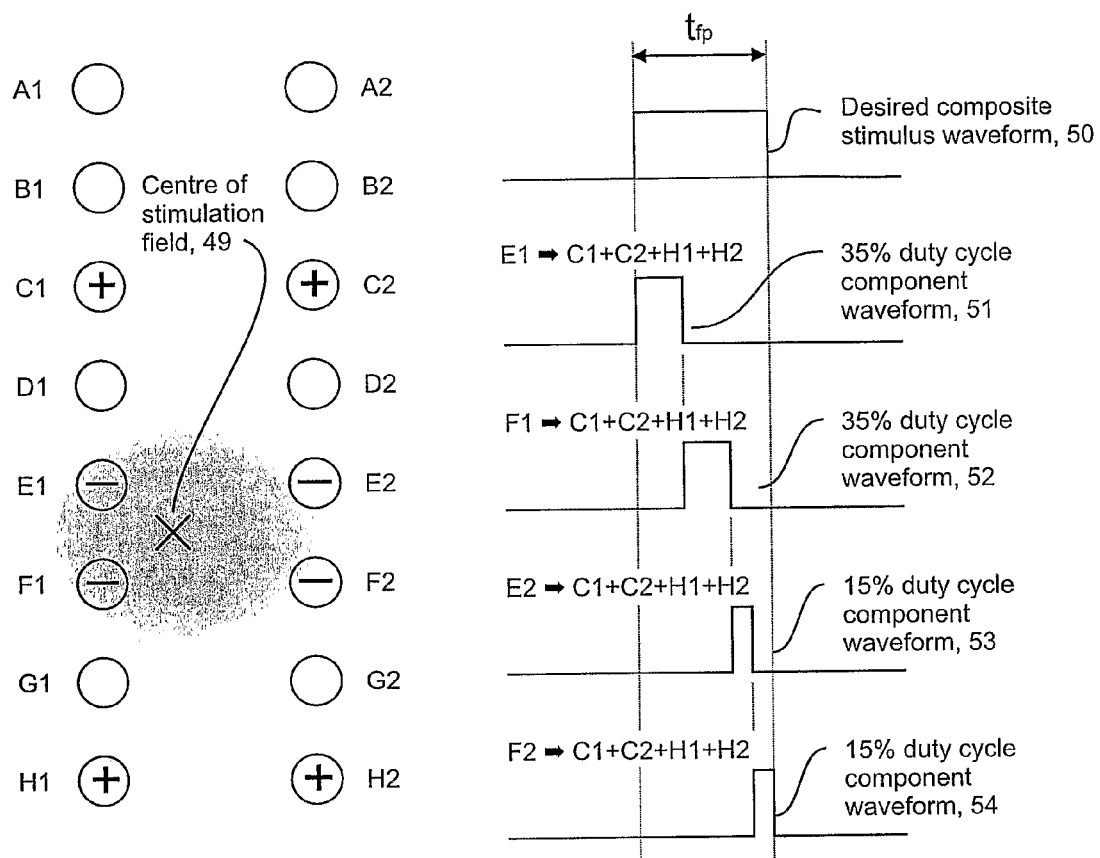
FIG. 11 shows an example of a side by side array of sixteen contacts together with the basic component waveforms (the low amplitude recharge or recharge pulse is not shown).

FIG. 11 illustrates another arrangement of electrodes, consisting of two arrays of eight electrodes side by side. This arrangement is useful for instance as a treatment of bilateral pain in spinal cord stimulation applications. In the example, four cathodes: E1, F1, E2 and F2 are used with a duty cycle (percentage of the stimulus waveform, 50) of 35% on E1, 35% on F1, 15% on E2 and 15% on F2. The resulting bias towards a higher duty cycle on the left electrodes to produces a stimulation field with a centre of stimulation that lies in to the centre left of the geometric centre of the four cathodes. The selection of anodes has a lesser influence on the perceived stimulation pattern, in this example the anodes are C1, C2, H1 and H2, and are connected in parallel by the switching matrix in the stimulator device. The component waveforms, 51, 52, 53 and 54 are applied in sequence to the four cathodes. In this example, it can be seen that a similar result could be achieved by applying a 70% duty cycle waveform to E1 and F1 connected in parallel, and a 30% duty cycle waveform to E2 and F2. In practical applications, there is seldom a unique solution to the component waveforms and electrode pairing given a desired stimulation pattern and centre of stimulation.

The previous figures are based on the assumption of a waveform with a forward negative pulse and low amplitude recharge pulse as discussed. An alternative approach is to use a bi-directional balanced waveform consisting of equal forward and reverse pulses as previously discussed and illustrated in FIGS. 1 and 6. In these cases the anodes and cathodes effectively reverse every half cycle. Preferably, the waveform has an inter-pulse spacing ($t_{ip}$ in FIG. 1) that is selected so that the reverse pulse and forward pulses are equally spaced in time. With a balanced bi-phasic waveform, the preferred method is also to couple pairs of electrodes, or small groups, rather than have a number of anodes connected in parallel at one time. This provides more precise definition of the current path between the electrodes and therefore better control of the location and coverage area of the composite waveform. FIGS. 12 to 15 show an example of such a system implemented in an array consisting of two rows of eight electrodes.

Figure 12A:
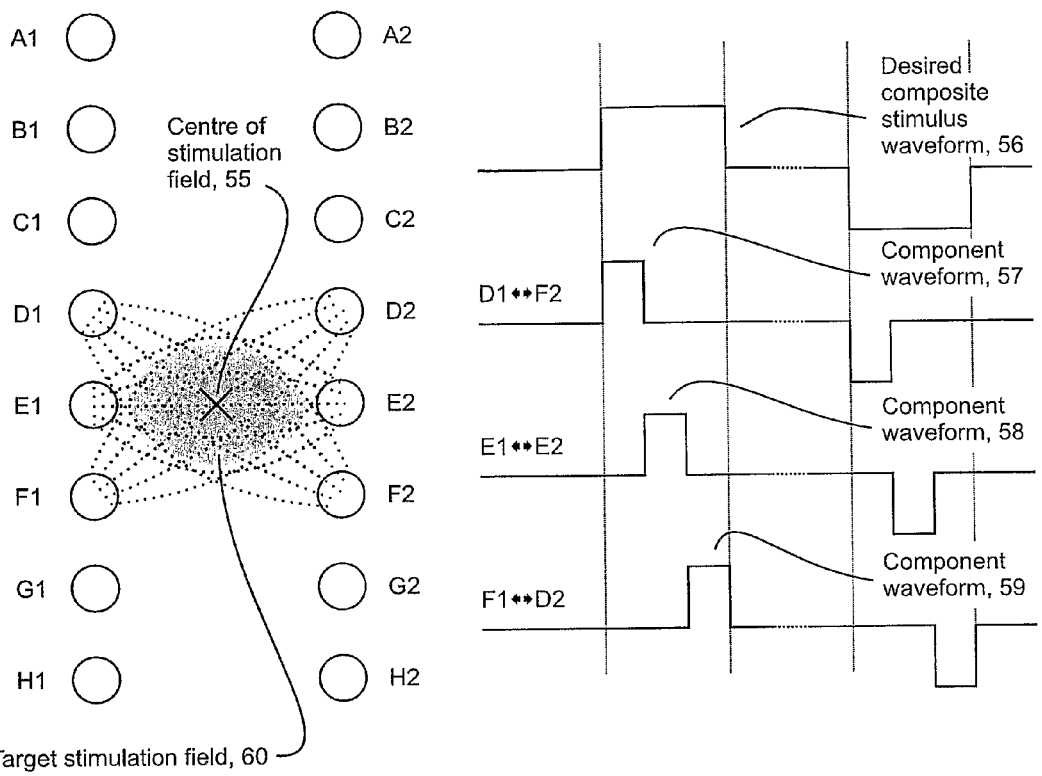
FIG. 12*a* shows an example of a focused stimulation field produced by a composite pulse using six electrodes (three electrode pairs) from an implanted array of sixteen contacts together with the associated component waveforms (the inter-pulse space not shown to scale).
Figure 12B:
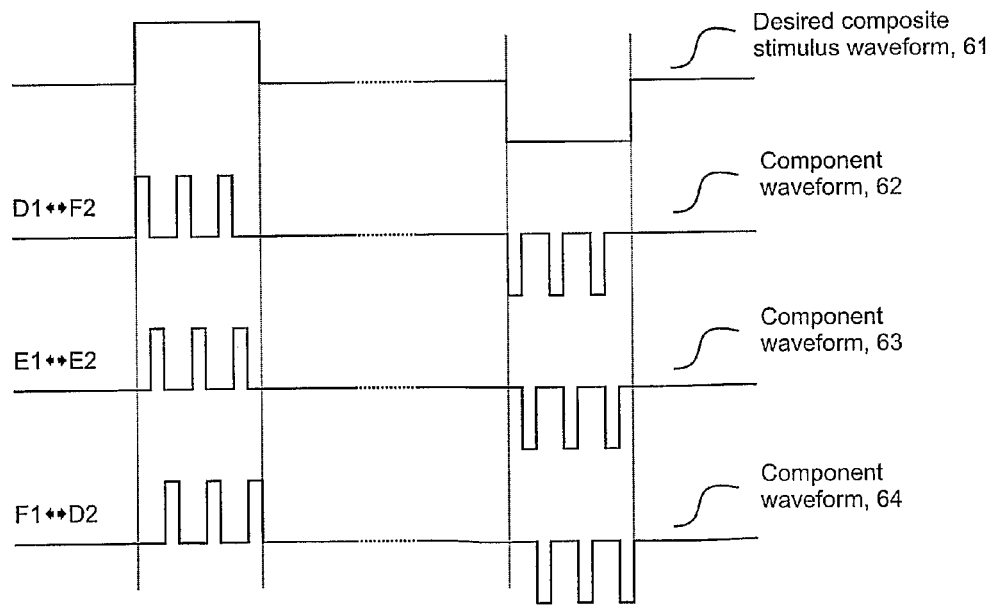
FIG. 12*b* shows alternate high frequency component waveforms (with the inter-pulse space not to scale) for the arrangement shown in FIG. 12*a*.

Referring to FIG. 12, the centre of the stimulation field, 55, is marked by the cross. The desired composite stimulus waveform, 56, is broken up into three component waveforms, 57, 58 and 59. As previously discussed, these waveforms may represent either current, voltage, energy or charge depending on the type of output driver used in the stimulator. The component waveforms are fed respectively to electrode pairs: D1-F2, E1-E2 and F1-D2. The target area of tissue is indicated by the shaded region, 60. The component waveforms in FIG. 12a illustrated are three pulses each accounting of 33% of the composite pulse. In practice, as previously discussed, it is preferable to further subdivide the component waveforms into a series of shorter pulses with the same total duty cycle, delivered in a train as illustrated in FIG. 12b.

FIG. 12 illustrates a focused stimulation field; it has a relatively low coverage area as a proportion of the area of tissue covered by the entire array.

Figure 13:
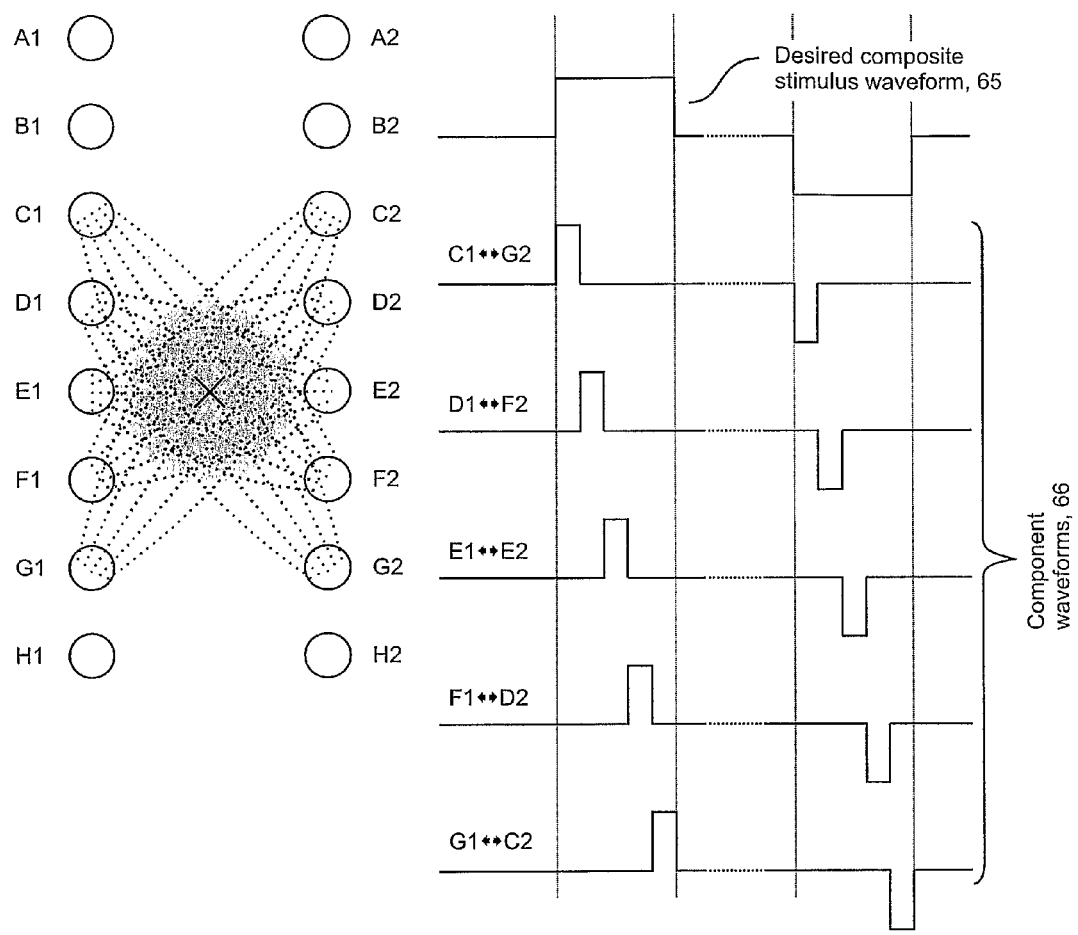
FIG. 13 shows an implanted array similar to FIG. 12*a* with ten electrodes (five electrode pairs) activated to produce a more diffuse composite stimulation field than FIG. 12*a*.

If a less focused stimulation field is appropriate, this may be achieved by recruitment of two additional electrode pairs, C1-G2 and G1-C2, as shown in FIG. 13. This causes the notional stimulation field to spread along the vertical axis. In this case, five component waveforms, FIGS. 13, 66, are derived from the composite waveform, 65, and applied to the five electrode pairs: D1-F2, E1-E2, F1-D2, C1-G2 and G1-C2.

Figure 14:
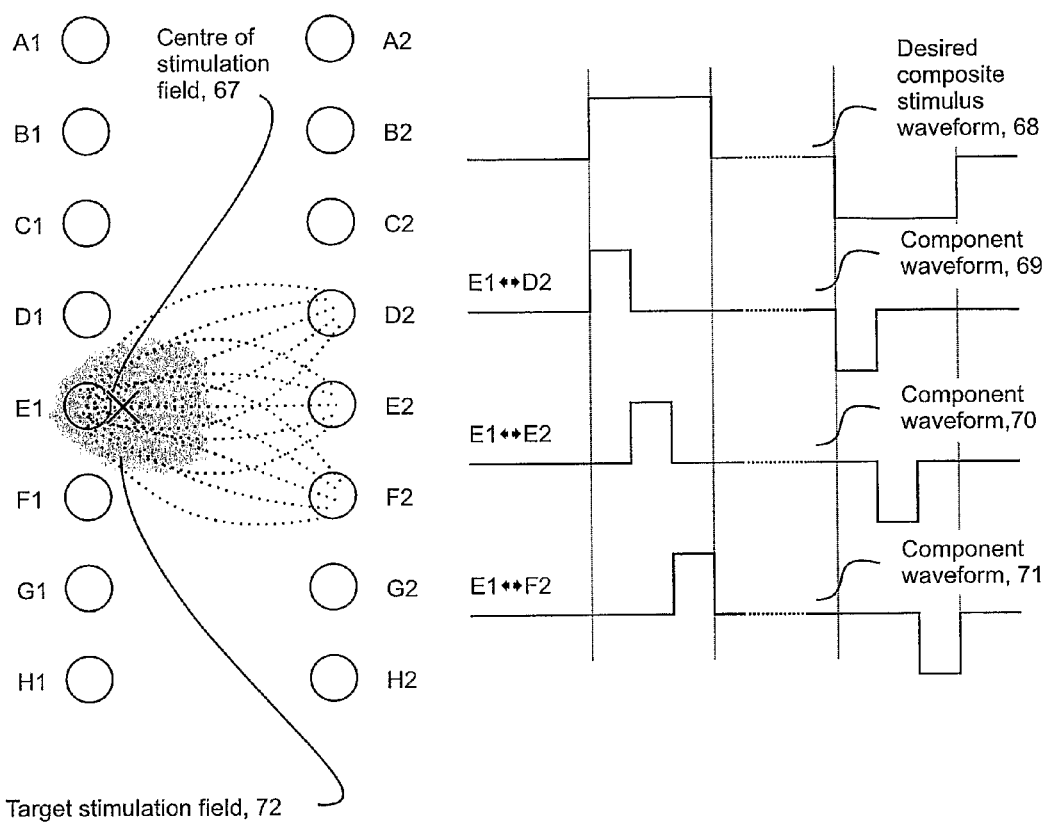
FIG. 14 shows a composite stimulation field centred over electrode E1 on the left side of the array.

Now assume that the centriod of the stimulation field in FIG. 12 should be repositioned to the left. FIG. 14 shows three component waveforms, similar to FIG. 12, but differs from the two previous figures in that one electrode, E1, is part of the electrode pairing in all three component waveforms. Consequently, this electrode carries current for the full duration of the composite pulse, 68, whereas the other three active electrodes, D2, E2 and F2 carry current for only 33% of the time.

The FIGS. 12, 13 and 14 can be considered to be three "reference" stimulation patterns, representative of three specific cases, i.e. focused stimulation in mid-line of the array, distributed stimulation in the mid-line of the array and focused stimulation to one side of the array.

In practice, the surgeon or patient preferably should not be concerned with the specific electrodes and component waveforms that are used to generate the stimulation pattern. These should be derived automatically from high level input of the desired location and coverage area of the stimulation field using an intuitive user interface.

In the case of sequential delivery of the component pulses, as illustrated in many of the preceding figures, it is reasonable to assume that the various reference stimulation fields described in FIGS. 12, 13 and 14 can be added together or interpolated to produce a desired field that represents an intermediate case.

Figure 15:
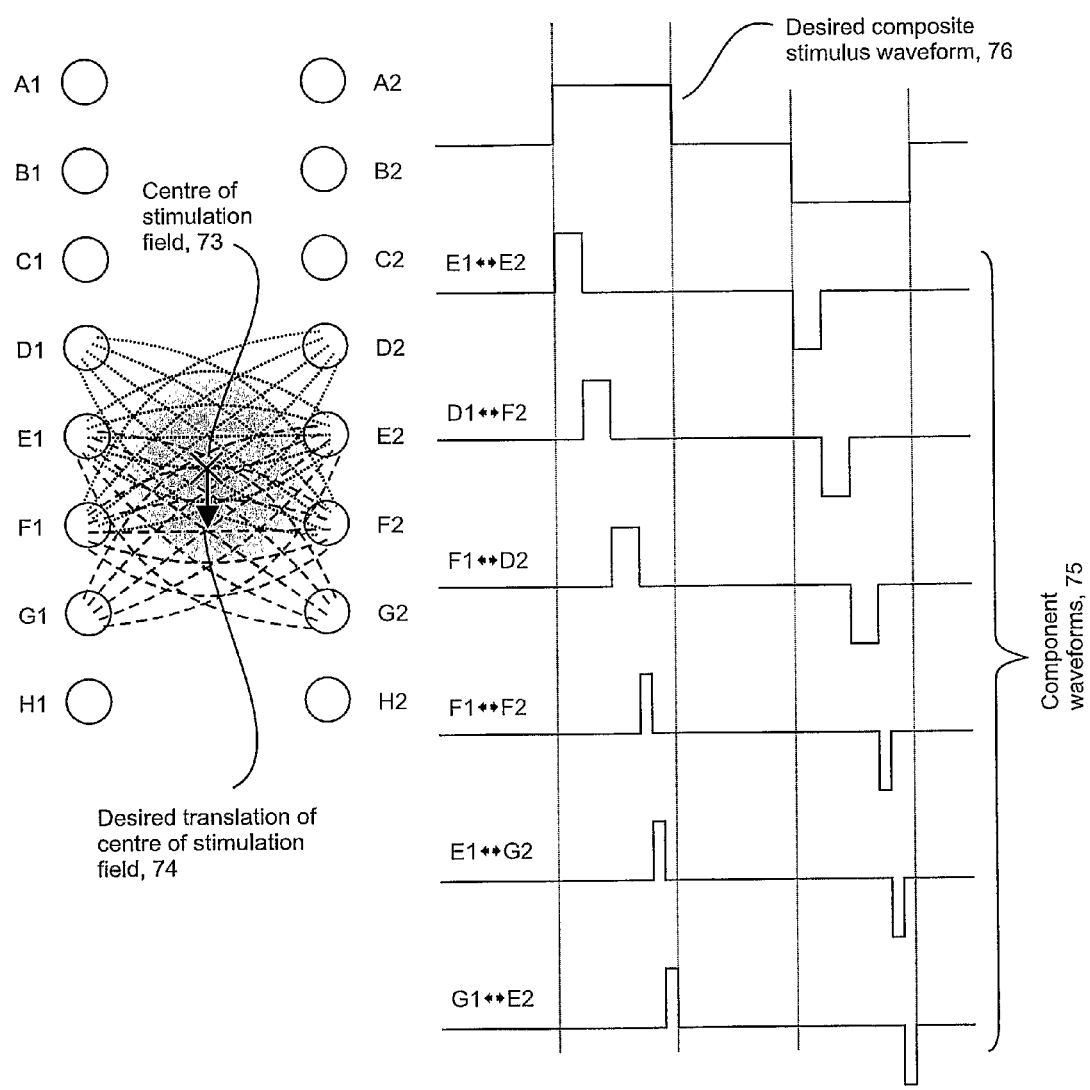
FIG. 15 shows a stimulation field generated by two groups of electrodes, group one: E1-E2, D1-F2, F1-D2, group two: F1-F2, E1-G2, G1-E2, activated in sequence.

FIG. 15 illustrates one such intermediate case. In this example, the surgeon has commanded the centre of stimulation, 73, to reposition along the midline of the array in the direction indicated by the arrow, 74. This may be achieved by duplicating the group of six electrodes first illustrated in FIG. 12 (electrode pairs D1-F2, E1-E2 and F1-D2 illustrated by the dotted lines showing current path) at a distance one pitch down on the array of electrodes (i.e. electrode pairs E1-G2, F1-F2 and G1-E2 illustrated by the dashed lines showing current paths). The duty cycle is then divided between these two respective groups in proportion to the desired displacement of the centre of stimulation. The resulting six component waveforms, 75, are shown in FIG. 15. It will be noted that as in the previous example, one electrode may form part of one or more pairings to produce the desired stimulation field. Furthermore, as before, if any component waveform contains pulses that exceed the maximum desired pulse width (typically 2 μs, or 4 μs, or 10 μs, or 20 μs, or 50 μs) they are preferably further subdivided by breaking each component into equivalent sub-component pulse trains of the same duty cycle as shown in FIG. 12b.

The preceding figures deal with only one configuration of electrode array and a limited number of ways of pairing the electrodes within that array. Other combinations are possible, for example the current paths need not cross as in FIGS. 12 to 15, but might consist of a ladder arrangement of electrode pairs such as D1-D2, E1-E2, and F1-F2. Furthermore, it is preferable in some instances to use the enclosure of the stimulator (FIGS. 8, 19) as one of the electrode pairs. This produces a stimulation field that tends to penetrate further from the site of the electrodes thereby allowing tissues some distance from the implanted array to be stimulated. The described method of controlling the stimulation field by means of component waveforms is equally applicable to this configuration.

If available, the stimulator enclosure is also a useful electrode for measuring contact impedance. Typically, contact impedance is measured by applying a known current or voltage to the enclosure and measuring the corresponding voltage or current for each electrode in turn. Similarly, impedance can be measured between specific pairs of electrodes. One advantage of using the enclosure as one electrode for sensing impedance is that a high precision current sensor can be implemented on this one output, which does not need to be duplicated on the other multiple outputs. If the enclosure is not used in the array, a high value sense resistor is one option. The enclosure output may also employ AC sensing current, either sinusoidal or square wave. This eliminates measurement error due to differing electrode potentials of the metals in the enclosure and electrode contacts.

Contact impedance may change over time as scar tissues build up around the implanted electrodes. In the figures, component waveforms have been based on the assumption that each electrode has the same quality of contact with the tissues. Where variations in contact impedance are observed and in particular when the composite pulse is a voltage output, it may be appropriate to vary the ratio of applied duty cycles to the electrode outputs so that different impedances are compensated. This process is referred to as normalisation.

A further application of normalisation is related to sensation. In both current and voltage controlled systems, it is preferable that each electrode is calibrated with respect to the enclosure electrode, so that all electrodes produce a similar level of perceived sensation at maximum output. To achieve this, each output in turn is activated and the patient adjusts the output so that it feels similar to the others, these relative settings are stored and used to normalise the system by weighting the ratio of duty cycles of the component waveforms.

Preferably, the surgeon is provided with a computer based programming system that graphically depicts the electrode array(s) in use in their relative locations. The programming system should include a series of pages to facilitate set-up of the device, this should include as a minimum a set-up page, a diagnostics page, a stimulation page and a program creation page.

The set-up page allows basic parameters to be configured, such as: selection of pulse type (for example balanced forward and reverse pulses, or forward pulses with a slow recharge); use of the stimulator enclosure as an electrode; and the configuration of the array (e.g. single in line, dual in line, side-by-side, wide or narrow spacing and the various types of paddle lead configurations).

The diagnostics page reports on the status of the stimulator device, including parameters such as battery status, error log, serial number etc. It allows contact impedance to be measured, relative to the stimulator enclosure or any other group of reference electrodes. This measurement may be achieved by applying a current or voltage to the enclosure, and measuring the corresponding voltage or current on the electrode in question.

The diagnostics page also includes the aforementioned sensation normalisation test mode. One method is to apply a reference waveform to each electrode contact in turn, with the stimulator enclosure acting as the anode. The amplitude of the reference waveform is increased slowly until the signal is just perceptible to the patient. The relative amplitude on each electrode is then available if required to adjust the duty cycles during stimulation so as to normalise the level of sensation from each electrode. A second method for bipolar balanced waveforms is to apply the reference waveform between appropriate pairs of electrodes that are used to build up stimulation patterns. This second method may produce a more accurate result, but may involve many pairs of electrodes.

The diagnostics screen should also be able to display historical impedance and sensation normalisation data which is stored either on the programming system, the patient controller, or the stimulator. This allows changes over time can be tracked, which for example may be used to identify formation of up scar tissue around the electrodes.

Figure 16:
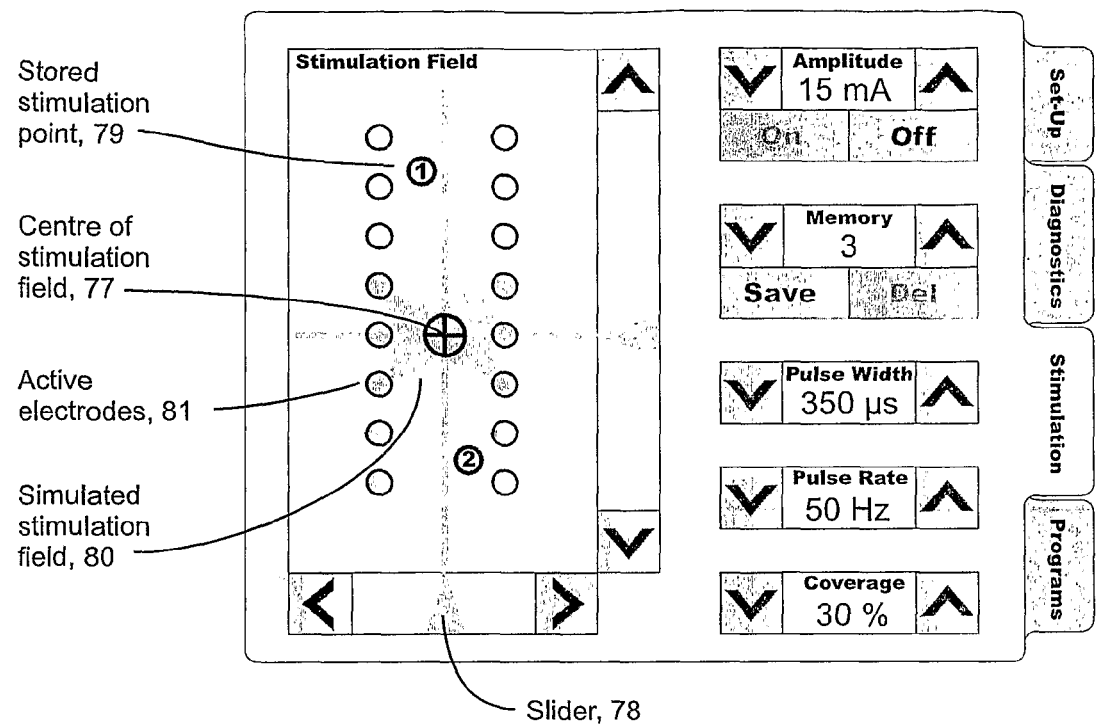
FIG. 16 shows an example layout of a touch screen from a computer based programming system for the stimulator apparatus.

The stimulation page allows the patient or surgeon real time control of the stimulation field and other key parameters. An example programming screen is illustrated in FIG. 16. This consists of a graphical representation of the array which changes to match the configuration of the implanted array, such as in-line and side-by-side. The page also allows control of often used parameters such as amplitude, composite pulse width, pulse rate and coverage area.

By means of a pointing device such as a mouse, touch screen, joystick or other such device the surgeon or patient directs the centre of the stimulation field, 77, on a graphical illustration of the array, using sliders, 78. The example shown is designed primarily for use on a touch screen but dedicated physical controls such as a joystick might also be used, with or without a display. The system provides a means of storing a series of stimulation points, 79, which are later combined using a program creation page into programs that define a particular set and sequence of stimulation points to achieve a desired therapeutic result.

The interface provides a graphical representation of the stimulation field, 80, and indicates which electrodes are active, 81. Optionally, the graphical display could use a external data source for the location of the array and the nearby tissue structures, for example an image of the spinal column and the actual implanted electrodes produced from a medical imaging system such as a Computed Tomography (CT) scanner.

The programming page allows stimulation points to be combined into treatment programs, which are preferably given names that are meaningful for the patient.

Once programming is complete, control of the implanted stimulator is provided by means of a patient controller with a small LCD or OLED or other compact display screen that may provide only basic control, such as selection of a program by name and control of the amplitude of stimulation. The programming unit and patient controller communicate with the stimulator device via wireless telemetry. In a preferred embodiment the patient controller (or the charging device for an implant) is provided with a USB interface that plugs into the programming unit computer. The patient controller (or charging device) then provides the wireless bridge to the implanted stimulator unit. Storage of programs may either be on the patient controller or the stimulator device. In the preferred embodiment programs are stored on the patient controller and downloaded to the stimulator device for execution as required.

Component waveforms are derived from data entered by the surgeon or patient input into the programming system. Key user entered parameters are: composite pulse width, centre of the stimulation field, coverage of the stimulation field, type of waveform required (i.e. with balanced forward and reverse pulses or slow reverse recharge), configuration of the electrode array, and the use (or not) of the stimulator enclosure electrode. In addition, the process requires assumptions to be made about electrical characteristics of the tissues.

Complexity of calculating component waveforms varies with the number of electrodes and physical arrangement of the array, the simplest being a linear array as illustrated in FIG. 10*a* with only the forward pulse to consider. In this case derivation of the component waveforms is a trivial task provided that the tissues are assumed to be homogeneous.

Complexity increases with the transcutaneous array illustrated in FIG. 3 and the implanted array illustrated in FIGS. 11 and 12. In more complex cases, there may not be a unique solution to a particular set of inputs.

In the preceding text, one method for calculating component waveforms is to use a set of reference stimulation fields such as those described for a side-by-side array in FIGS. 12, 13 and 14 which are added together or interpolated between to produce a desired field that represents an intermediate case. This method has a very low computational overhead, which is ideal for real-time control of the stimulation field such as required for the stimulation set-up page in the programming system described above.

An extension to the reference stimulation field method is to consider current paths from the electrodes in the array and arrive at combination of these paths that gives a best fit to the parameters input by the surgeon. Current paths may be calculated using a finite element model of the tissues, either in two or three dimensions.

By way of example, a finite element method for combinations of electrode pairs with sequential delivery of the pulses is described below. At its simplest, the finite element model consists of a two dimensional network of resistors of arbitrary value, either arranged as a series of squares or triangles with resistive elements on the sides of the elements and nodes at the n*m vertices. For each electrode pair in an array, a nominal current is applied and the resulting two dimensional current distribution produced by iteration based on the assumption that the currents flowing into and out of each vertex sum to zero, with the exception of those vertices that represent active electrodes in the array. Solution of this by iteration produces an n*m matrix which is a current distribution map containing current vectors at each point in the matrix for a specific electrode pair.

Figure 17A:
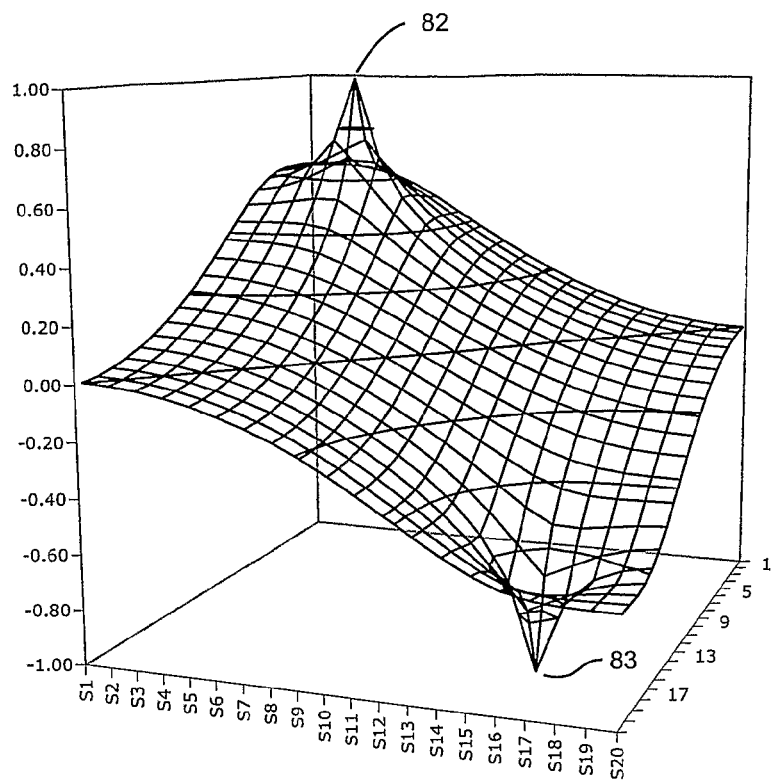
FIG. 17*a* shows a finite element model of current flows in a two dimensional homogeneous resistive medium, illustrating the voltage distribution.
Figure 17B:
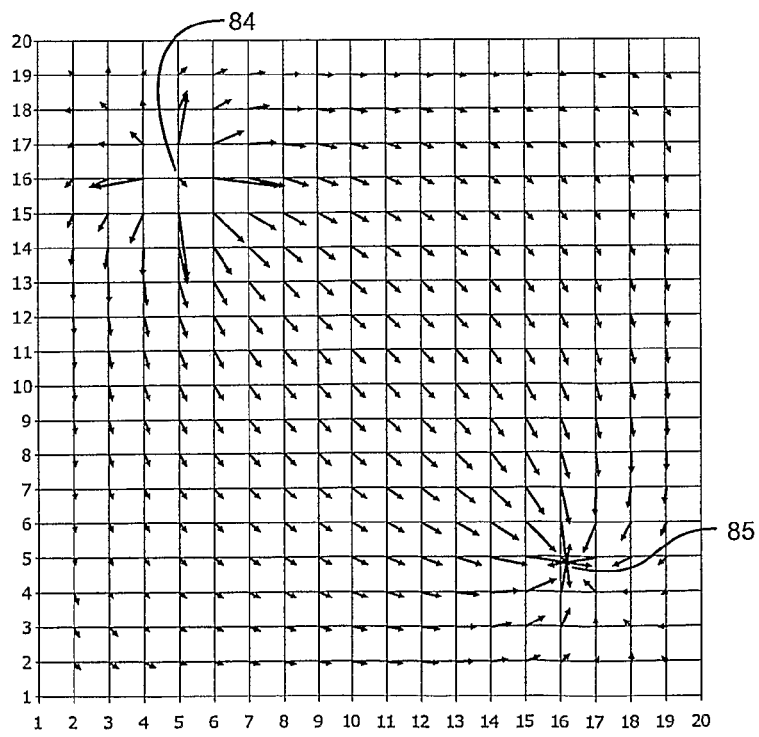
FIG. 17*b* shows current vectors associated with the voltage distribution in FIG. 17*a*.

A pictorial example of this is shown in FIGS. 17*a* and 17*b*. FIG. 17*a* shows the voltage distribution between two electrodes, with a +1 and −1 (82 and 83 respectively) unit voltage applied to the electrodes, based on a 20 by 20 element model with unity element-to-element boundary resistance and an infinite resistance between the edge elements and the outside world. FIG. 17b shows a vector plot of the current flow in the matrix, where each vector represents a direction and magnitude for the predicted current at the centre of each element. The two electrodes are denoted 84 and 85.

A library of matrices is produced for each electrode array, representing each pairing that may be employed. These matrices need not be calculated in real-time while the surgeon or patient moves the centre of stimulation, but can be pre-calculated and stored on the programming system computer. Derivation of the component waveforms is achieved by finding the values of the coefficients that define weighted sum of the available matrices that provide the best fit to the desired stimulation field. For example, if $[d_{ij}]$ is a matrix of dimensions n*m that defines the desired stimulation field and $[a_{ij}]$, $[b_{ij}]$ etc. are m*n matrices that define current distribution maps in possible electrode pairings, we find the values of the coefficients $x_1$, $x_2$ etc. that satisfy:

$$[d_{ij}] \approx x_1[a_{ij}] + x_2[b_{ij}] + x_3[c_{ij}] \ldots$$

The coefficients $x_1$, $x_2$ etc. represent the relative duty cycle or amplitude used for each corresponding component waveform. Modern microcomputers are sufficiently powerful to solve this using heuristic techniques in real-time.

It can be seen that this method is applicable to combinations of multiple electrodes as long as a current distribution matrix is produced for each combination, e.g. a single cathode and multiple anodes, or where multiple electrode arrays are used together, e.g. two linear arrays implanted in a line. It will also be appreciated that the above method is one of a number of analytical and numerical methods that may be employed to find a solution for the component pulses.

As discussed above, a diagnostic screen is provided in the programming system. One output from the diagnostic system is the electrode contact impedances with reference to the stimulator enclosure. In a system without closed loop control of charge or current, the contact impedance may be included in the calculation of each current distribution map, these maps calculated by the programming system when the stimulation set-up page loads.

Also provided in the diagnostic screen is normalisation of sensation on each contact. As previously discussed this information can be used if desired to modify the various duty cycles in an attempt to normalise the sensation levels produced by each electrode pair. An alternative approach is to use the information to modify the matrices so that they represent "sensation maps" rather than current distribution maps.

The finite elements can be adapted so that they are not purely resistive, but include for instance the effects of polarisation of tissues. The resulting component waveforms may produce stimulation patterns where adjacent pairs are excited in alternate polarities to focus the desired current path.

Clearly, the finite element model can be extended further to include an anatomical model of the electrical characteristics of the tissues in two or three dimensions. This is achieved by mapping the electrical characteristics of the tissues onto each element in the model.

Figure 18:
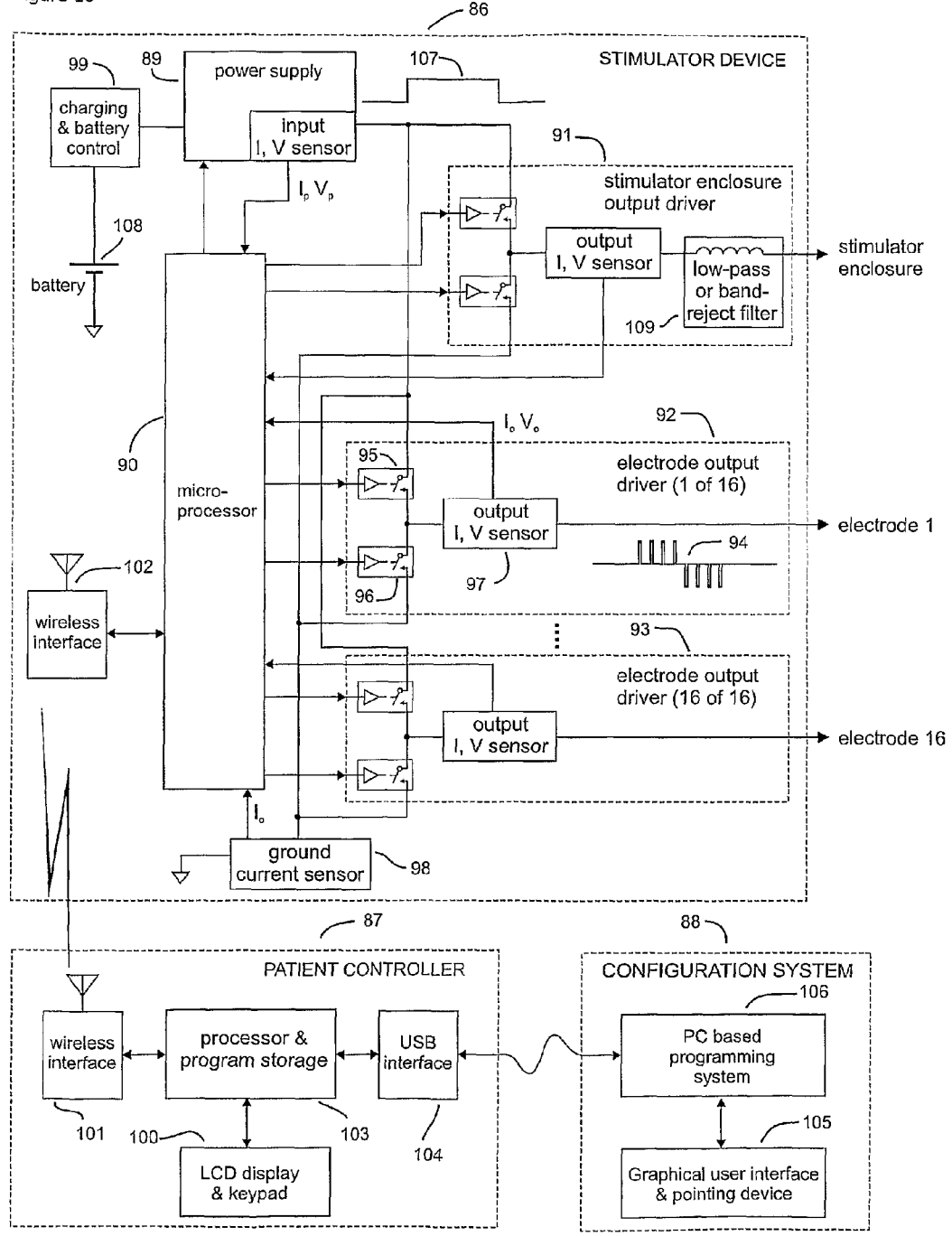
FIG. 18 shows a block diagram of the apparatus.

FIG. 18 shows a block diagram of a typical implanted apparatus according to the invention. The apparatus consists of three sub-systems, the implanted stimulator device, 86, and patient controller, 87, and the configuration system, 88.

The stimulator device, 86, consists of a power supply, 89, controlled by a microprocessor system, 90. The power supply takes energy from the batteries, 108, and under control of the micro-processor, 90, produces an appropriate current pulse or voltage supply to produce the desired composite pulse, 107 (this example illustrating current from a unipolar supply). The power supply can be either a single polarity output (for example a current or voltage source) or it can be a dual polarity output able to sink and source current. In a preferred embodiment for an implanted device, the power supply is a switch-mode circuit operating from a rechargeable lithium ion battery of nominal voltage 3.6V, producing either a current or voltage controlled output. In the case of a current supply, the micro-processor commands the power supply to produce a composite current pulse, the amplitude of which may be variable up to a maximum typically 20 mA, but limited by a maximum output voltage of 15 V. In the case of a voltage supply, the micro-processor commands the power supply to produce a voltage which may be of variable amplitude up to a maximum of typically 15 V peak, but limited by a maximum output current of 20 mA. In the voltage controlled case, the voltage itself need not be pulsed—the composite pulse, 107, is a current pulse formed by the sum of all currents drawn by the output stages. In both cases, the microprocessor controls the power supply and the output stages so that its desired composite stimulus pulse appears on the output of the power supply.

A number of output stages (e.g. 91, 92 and 93) are provided to form the component pulses, 94. Typically, sixteen or seventeen outputs are provided, of which only three are shown in the figure. Sixteen outputs (of which all are identical but only two, 92 and 93, are shown) are used to drive sixteen electrode contacts via two eight way connectors on the top of the stimulator device, and a seventeenth output, 91, is used to drive the stimulator enclosure. Each output stage consists of a high and low side switching element (termed a "totem-pole" output), 95 and 96, which is controlled by the microprocessor and provides a tri-state output: connected to the pulse generator, connected to ground, or high impedance with both switching elements off.

If the stimulator has a single polarity pulse generator, the high and low side switches only have to conduct current in one direction, so each may comprise a single transistor. With a bi-directional dual polarity supply, the switches need to conduct current in both directions and therefore may comprise back-to-back P and N channel transistors.

With a bidirectional supply, the seventeenth totem-pole output, 91, for the stimulator enclosure is not required. Instead, the enclosure is connected via the low pass or a band-reject filter, 10, and a single switching element, so that it may be high-impedance if required.

The output drivers (91, 92 and 93) synthesize component waveforms, 94, under control of the microprocessor, 90, by connecting the appropriate electrode pairs in turn in the appropriate polarity thereby directing the composite stimulus pulse, 107, to the electrode pairs in sequence. Individual component pulses are preferably short, less than a maximum of 50 μs or 20 μs or and more preferably less than 10 μs 4 μs or 2 μs, so high speed switching elements 95 and 96 are required.

The level of current, $I_p$, and voltage, $V_p$, applied to the outputs via their respective switching elements are measured by voltage and current sensors in the pulse generator circuitry, 89, and fed back to the microprocessor. Because the microprocessor controls the electrode pairs in use at any moment, this data may be used to calculate contact impedance, identify wire breaks, etc. It may also be used to check that forward and reverse current flows are matched, which is an important safety feature in a DC-coupled stimulator device. As previously discussed, unbalanced bidirectional waveforms may cause undesirable migration of ions in the tissues to one electrode; additionally this may also play a role in long term electrode decomposition. However, it should be noted that even though balanced forward and reverse charge is preferred, the invention is equally applicable to cases where there is a DC offset in the desired signal.

Each output stage may optionally be provided with an output sensor, 97, which measures output current, $I_o$, and output voltage, $V_o$, and feeds this back to the microprocessor. Typically the output sensor consists of a low ohm resistor in series with the output and a precision analogue to digital converter (A-D) which measures the voltage drop across the resistor thereby deriving current. For compactness, typically the A-D is multiplexed across the output channels.

In addition, the output sensor circuit may contain an integrator or a sample and hold circuit that measures the net current, or charge, on the respective output. This circuit may take discrete readings once or more times per component pulse, or accumulate the charge over each cycle, recording the magnitude of forward and reverse delivered charge to higher resolution than is readily achievable by sampling directly from the microprocessor.

Measuring current or charge in this way using analogue electronics is convenient as it offloads the requirement for fast data acquisition from the microprocessor. The microprocessor can then acquire the data from each output after the end of the cycle, in the relatively long time period between each waveform. The data may be used to control current, charge, or make adjustments in forward and reverse pulse duty cycles to correct ensure net zero charge delivery over the long term. An alternate approach (not shown) is to put a series capacitor in each output.

A more compact alternative to individual output sensors is to put a single ground current sensor, 98, in the common ground connection of all output drivers. The ground current sensor measures current flowing through the return path of the active electrode pair at any particular moment. The advantage of the ground current sensor is that only one is required, rather than duplicating the circuit on each output. Synchronisation of the sampling of the current sensors, both at the pulse generator and the ground or output is desirable to prevent measurement errors. Because of the short (sub-microsecond) duration of some component pulses it is ideal to synchronise sampling to occur just after the leading edge of each pulse. This data may either be sampled and stored digitally, which requires fast sampling and conversion, or a multiplexer may be used to store the data using analogue means for later conversion by the microprocessor.

Other methods are possible, such as a sensor in the ground leg of each totem-pole, this has the advantage that the sense resistors are referenced to ground, rather than floating as is the case with sense resistors in the outputs.

The microprocessor also compares measured currents (and voltages) on each output sensor, or the ground sensor, with those produced by the signal generator. This provides as a cross-check that the system is operating correctly, thereby providing an additional level of safety for the patient.

It has been noted that the sixteen outputs, e.g. 92 and 93 that drive the electrode array differ from the single output, 91, that drives the stimulator enclosure as the latter has a low pass or band-reject filter, 109, connected in series in the output. This is a passive resonant filter which is high-impedance to signals of the same frequency as the radio frequency (RF) signal produced by Magnetic Resonance Imaging (MRI) scanners, for instance 64 MHz for a 1.5 Tesla machine and 128 MHz for a 3 Tesla machine. The MRI RF signal causes a voltage to be developed along the stimulator leads that without the filter would induce current flow between the implanted electrode array and the stimulator case. These currents may be sufficient to cause heating of the tissues in the region of the electrode array well above the 2° C. limit that is considered acceptable by the US Food and Drug Administration. The advantage of this over filters in the outputs is that we only need one per stimulator, rather than one per output. However, in a variation of the apparatus, additional output filters are provided to isolate one of the eight way electrode connectors from the other, so that currents cannot also be induced to flow between the two leads during MRI.

The stimulator device also includes a battery, 108, and a battery control circuit, 99. If the battery is rechargeable, this circuit controls the charging sequence, using energy from magnetic, electromagnetic or direct electrical energy supplied to the implanted device by an external charging unit. The external charging device is not shown in the figure, but may be a separate unit, or form part of the patient controller, 87.

The patient controller is preferably pocket-sized and typically has deliberately limited functionality presented to the user. A small LCD or OLED display and keypad, 100, allows the patient to select one of a number of pre-defined treatment programs, start and stop treatment, control the overall amplitude of stimulation and check the battery status of the implant. The patient controller contains a wireless interface, 101, which can communicate with a similar interface on the stimulator device, 102. The wireless interface is preferably the established standard for communication with medical implants, the Medical Implant Communications Service (MICS). MICS is a low power radio service for transmitting data to and receiving data from implanted medical devices. In the preferred embodiment, treatment programs are stored in the patient controller processor, 103, and transmitted to the stimulator device only as required, which simplifies the firmware in the stimulator device thereby increasing reliability.

The configuration system, 88, is a PC-based system with a graphical user interface, 105, that provides the surgeon and/or patient with diagnostic and programming functions such as the creation of treatment programs as previously described. The configuration system communicates with the patient controller via universal serial bus (USB), 104. For simplicity, the patient controller is the only device that communicates directly with the implant. All instructions from the configuration system for the implant are interpreted by the patient controller microprocessor, 103, before transmission over the wireless interface.

It should be noted that the apparatus described in FIG. 18 cannot provide the full range of pulses that are possible according to this invention. The apparatus cannot produce component pulses that overlap as illustrated in FIG. 10e, for which an apparatus with one independent signal generator for each overlapping component pulse is preferred. An independent signal generator dedicated to each output is the most flexible configuration, but this is not the preferred approach for an implanted device because of size constraints. For an external stimulator, where size is less important, this may however be acceptable. The apparatus in FIG. 18 has the advantage for implanted applications that only one power supply is required, which can be designed to step up the battery voltage and synthesize the composite pulse in one step. The combined power supply and signal generator can be constructed using switch-mode techniques, which are energy efficient.

As previously mentioned, there are a number of options for the power supply. To summarise, these include:
  a) Fixed voltage or fixed current with control of the output amplitude by modulation of the pulse width of the component or sub-component pulse as a proportion of the duty cycle available to each pulse.
  b) Variable voltage or variable current.
  c) A combination of a) and b) above, such as with a limited dynamic range and relatively low bandwidth variable supply plus modulation of the component pulses and/or variation of the relatively duty cycles of these pulses.
  d) Unipolar or bipolar versions of a), b) and c).

For an implanted device, where space is at a premium, the ideal high bandwidth switch-mode current source is not readily achievable.

A practical compromise is a variable voltage, switch mode supply of relatively low bandwidth, together with modulation of the pulse width of the component or sub-component pulses to provide additional high bandwidth of control of the effective amplitude of each pulse (option c) above). The system includes feedback of the current flowing in each component or sub-component pulse by either sampling the current at a particular point in the cycle (typically just after the leading edge) or accumulating the average current over the pulse by means of an integrator. The latter is preferable, and as previously discussed may be performed either in the output sensor, 97, or in the power supply, 89, or ground current sensor, 98. An alternative is a switch-mode voltage source driving an analogue high bandwidth current source. The switch mode voltage source is efficient but relatively low bandwidth, but provides only the minimum voltage headroom to the analogue current source which is able to provide a high-bandwidth, stable output within the confines of the headroom voltage available.

In a compact apparatus, duplication of the current sensing for every output may not be practical, so the output sensors, 97, are not implemented, but are replaced by the ground current sensor, 98, which is cross checked against an input sensor built into the power supply and pulse generator, 89. This allows current control to be implemented on a pulse-by-pulse basis, to compensate for changes in output impedance. It also allows contact impedance to be measured on an ongoing basis; this data is stored in the stimulator device and may be fed back to the programming system or used to raise an alarm in the event of a rapid: change of impedance on a particular contact.

The power supply in the embodiment above is unipolar, the output switch matrix inverts the polarity of the output as required. Because of the unipolar supply, each totem-pole output driver need consist only of a high and low side mosfet driven via level translation circuitry from the microprocessor. Such a configuration has minimal component count. It is capable of non-overlapping component pulses, delivered sequentially, such as those illustrated in 10b. It will also produce component pulses with an interpulse spacing, such as illustrated in FIG. 10c. With voltage control, the signal generator maintains the desired output voltage for a period equal to the sum of the component pulse and their interpulse spaces.

The bandwidth of the voltage controlled power supply does not have to be high enough to change amplitude which each component pulse, but should be sufficient to allow the output amplitude to be reduced so that the amplitude can be changed every cycle to allow cycle-by-cycle control of current or charge, and also to allow reverse recharge pulses of low amplitude to be produced, such as illustrated in FIG. 7.

Returning to FIG. 18, MRI is an extremely valuable diagnostic technique, but is contraindicated in many implanted stimulator applications because excessive electrode heating has been known to cause permanent injury or death. The degree of electrode heating is however difficult to predict since it varies with the physical arrangement of the lead wire, placement of stimulator unit, the characteristics of the tissues surrounding the electrodes, orientation of the patient to the magnetic and RF fields, and many other factors. For cases where MRI compatibility is considered to be of paramount importance, a pulse generator with precise current or voltage control, 89, together with output sensor, 97, or other precision sensing of current and voltage, may be used in combination with a specialised electrode lead to measure electrode temperature during MRI imaging.

To maintain connector compatibility with a standard eight contact lead, one embodiment of a specialised temperature sensing lead differs from a standard eight electrode lead in that it has fewer electrode outputs and dedicates the remaining outputs from the stimulator unit to temperature sensing. For example, a paddle style lead might have four electrode contacts. Each electrode is formed from an inert biocompatible material such as Platinum-Iridium. An insulating substrate, typically a ceramic material, is bonded on the underside of one or more of the electrodes. On the back of the substrate, a thin film of Platinum is deposited on the surface which is formed into a fine serpentine shape using photolithographic techniques to produce a resistance temperature detector (RTD). The RTD relies on the changing electrical resistance of platinum with temperature. Typically, it is laser trimmed so that nominal resistance at 0° C. is for example 100Ω. The RTD exhibits an approximate change in resistance of 0.4 Ω/° C., but the relationship is not quite linear and results in a nominal resistance of 114.382Ω at a body temperature of 37° C. The RTD thus formed has the advantage that it may be constructed completely using known biocompatible materials.

Figure 19:
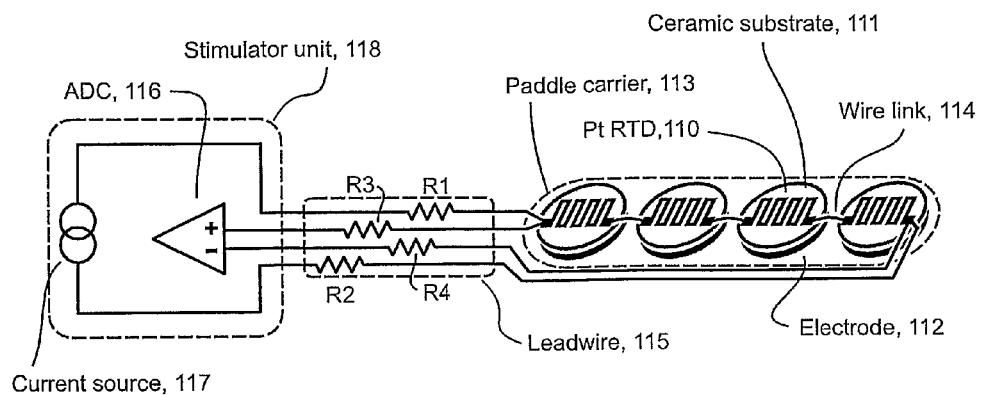
FIG. 19 shows a paddle lead with embedded temperature sensing.

An diagrammatic example of such a lead and its interface to the stimulator unit is shown in FIG. 19. Each of four electrodes, 112, has a ceramic substrate, 111, bonded on the back on which a thin-film platinum RTD, 110 is constructed. The RTD is hermetically sealed to prevent moisture contamination by means of a ceramic or glass covering layer (not shown) which is fused in place. The electrode contacts are shown in the diagram with their tissue contact face facing downwards and out of view, and the four wires from each contact to the stimulator unit have been omitted for clarity.

The RTD may be present on just one of the four electrodes, or as illustrated may be repeated on each electrode and connected together using wire links, 114, so that the average temperature of the four electrodes is measured. The paddle electrode assembly is held together by a flexible insulating carrier, 113, shown in outline.

The lead wire, 115, contains eight individual insulated wires (including the four electrode contact wires not shown). Each of the resistors, R1, R2, R3 and R4 are representative of the resistance of the sensing leads, which is typically 3-4Ω.

A safe limit for electrode heating is 2° C., so precision temperature measurement is desirable. To compensate for resistance of the wire that connects the RTD to the stimulator unit and also to compensate for contact resistance in connections between the two, a four wire connection to the RTD is used in this example. In a four wire arrangement, two wires are used to carry the sense current provided by the current source, 117, and two additional wires are used to measure the voltage across the sensor element, measured by an analogue to digital converter, 116. The sense current is typically 1 mA or less, as a higher current causes self-heating of the sensor. The voltage change on the sensor with a 1 mA sense current is small, nominally 386 μV for a one degree change from 37 to 38° C. (assuming that the nominal resistance of the RTD at 0° C. is 100Ω).

Referring to FIG. 18, it is possible to use available stimulation outputs to make measurements with the temperature sensing lead by incorporating a precision analogue to digital converter for measurement of voltage and/or current (preferably synchronised acquisition of both) in the output stage, 97, or in the power supply, 89, preferably with 16-bit or better resolution. This does however mean that precise control of the output current or voltage from the pulse generator is desirable, which may increase complexity.

In order to increase resolution, the sense current may be increased to 10 mA or more provided that current is only applied for a few microseconds each time a reading is taken, so that self-heating is minimised.

Wire wound platinum RTDs are also suitable temperature sensors for implanted leads. In these sensors very fine platinum wire is coiled over a glass rod, or a coil is preformed, inserted into a ceramic tube and sealed to prevent moisture ingress. The sensor may be produced in diameters small enough to fit inside the end of a percutaneous lead, such as illustrated in FIGS. 9a, 23.

High frequency noise from the MRI RF subsystem (e.g. 64 MHz at 1.5 T) and lower frequency noise from the gradient coils (e.g. approximately audio frequency repetition rates with higher edge rates) may cause voltages to be induced on the wires connecting the RTD to the pulse generator. Therefore, it is preferable that low pass filters are provided on the inputs to the analogue to digital converter to remove these high frequency components.

Because of the small resistance change in the sensor that must be detected and the high level of electro-magnetic interference from the MRI system, an additional approach is to take readings only in quiet periods between RF bursts and when the gradient coils are inactive, or to sample continuously but ignore readings that are clearly incorrect due to such noise. Consequently, during an MRI procedure, the stimulator device monitors induced voltages on the electrode leads by periodically sampling the voltage and takes temperature readings only during quiet periods. A series of readings are taken at each sample to allow averaging and as a cross-check that there is no significant electro-magnetic interference. The stimulator unit transmits the temperature information to the patient controller via wireless telemetry, or transmits an error message if no reading is possible after a specific timeout period. The patient controller either displays electrode temperature or transmits this information to another device that is visible to the MRI operator. In the event of a dangerous rise in electrode temperature, an alarm may be sounded and the MRI procedure terminated, the procedure interrupted to allow the implanted electrodes to cool to a safe temperature, or the patient repositioned in the scanner so that coupling between the MRI RF fields and the leads is minimised.

As discussed, four wires provide the highest precision for a single RTD sensor. Typically, a specialised temperature sensing lead has eight contacts on the stimulator connector for compatibility with non-sensing leads, but has only four electrode contacts, with four wires reserved for the sensor. In addition, a fifth wire may be provided by utilising the clamp contact (FIGS. 9b, 29). With five leads available it is possible to independently sample two RTDs connected in series. These may be used to measure the temperature of two of the four electrodes in the array, or four series-connected RTDs on the back of each electrode contact may be used, with the stimulator device sensing the average temperature on two groups of two electrodes.

An alternative arrangement is a three wire configuration, where two wires are connected to one side of the RTD and this is used to make a correction for wire resistance on the assumption that the wire that connects to the other side of the device is similar.

Another alternative is a two wire arrangement in which the sense current is supplied and the voltage measurement is made on the same two wires. The disadvantage of this approach is that absolute temperature measurement of the electrode tip temperature is not as reliable because the resistance of the leads and electrical contacts are not easily compensated. Nevertheless, this circuit can provide high resolution information concerning the change in the temperature of the electrode tip during an MRI procedure, provided lead and contact resistance can be assumed to be constant, which is a reasonable assumption over the short time periods of interest. The two wire arrangement is the preferred embodiment for the reasons described below.

As previously discussed, it is desirable that connector compatibility is maintained with a standard eight contact leads, so a standard stimulator device may be used with sensing and non-sensing leads. Therefore, the standard non-sensing lead, illustrated in FIG. 9b, is arranged so that the free end is long enough to incorporate one additional contact.

Figure 20A:
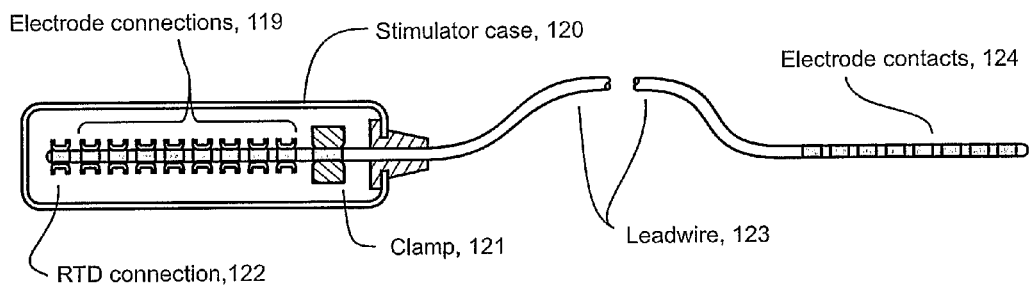
FIG. 20*a* shows an overall arrangement of a percutaneous lead with embedded temperature sensor.

FIG. 20a illustrates an example of a percutaneous lead with embedded temperature sensor with a two wire sensing arrangement. A ninth contact, the RTD connection, 122, is added to the end of the lead. The clamp, 121, is used as the other RTD connection. Consequently there are ten connections in total to the lead wire, 123, and eight contacts are now available for stimulation electrodes, 124. Because two additional wires are dedicated to the RTD interface, no internal isolation or switching circuitry is required in the stimulator unit.

Figure 20B:
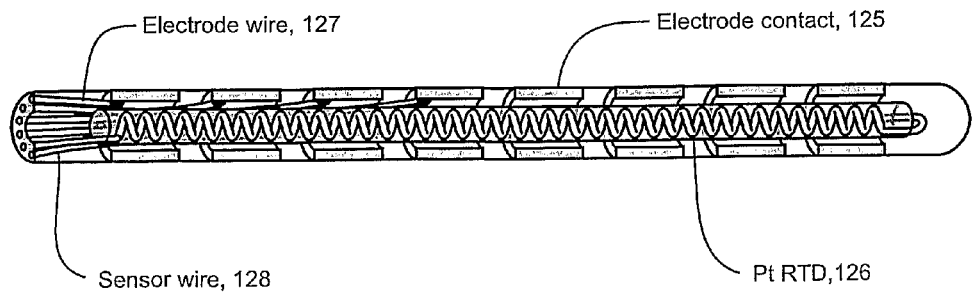
FIG. 20*b* shows a section through the electrode contacts of the above percutaneous lead with embedded temperature sensor.

In this example of a percutaneous lead with temperature sensing, a wire wound platinum RTD is employed. FIG. 20b shows a section through the end of the lead. The eight electrode wires, 127, and two sensor wires, 128, are embedded in the lead. The lead itself is hollow so that a stiffening guide wire can be inserted to aid positioning during implantation. At the end of the lead the electrode wires (of which four of the eight are shown in the sectional diagram) are welded to the inside of each electrode contact, 125. A coiled platinum RTD, 126, sealed from moisture ingress, is positioned inside the electrode array in good thermal contact so that it can measure heating of the contacts. The entire assembly is approximately 1.3 mm in diameter.

Prior to an MRI procedure, the two wire RTD circuit is calibrated against another temperature sensor internal to the stimulator unit, or zeroed on the assumption that normal body temperature is stable, or calibrated against a reading of body temperature taken by the clinician. During the procedure, the change in RTD value is used to trigger an alarm if the tip temperature rises by a preset amount, typically 2° C. Because the RTD in this example measures the average temperature of all eight electrodes, the alarm may be set at a lower value in case of one electrode changes temperature more rapidly than the others, although generally this is not the case as all electrodes and their corresponding wires have a similar coupling to the external fields.

Figure 21:
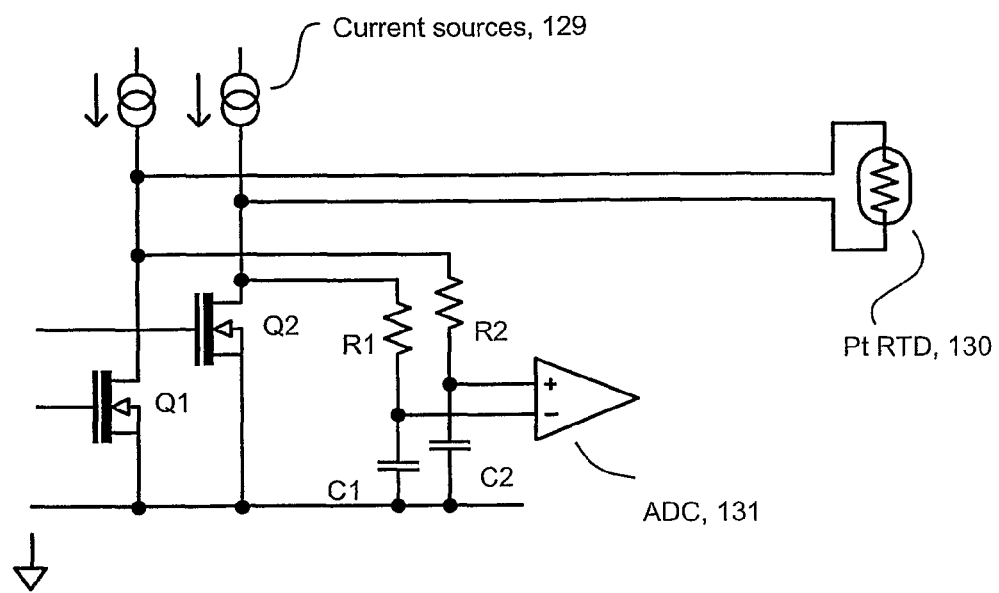
FIG. 21 shows a two wire resistance temperature device interface.

FIG. 21 illustrates an example implementation of an interface to the RTD sensor in the stimulator unit. This circuit uses two current sources, 129, to apply a known sense current in both forward and reverse directions across the RTD, 130. Differencing forward and reverse voltages compensates for low frequency induced noise and DC offset due, for example, to dissimilar metal junctions in the connectors or wiring.

In this example circuit, the two current sources are provided by two high precision (0.1%) 15 kΩ resistors connected to a stabilised 3.0V supply. The RTD has a nominal resistance of 500Ω at 0° C., which corresponds to 571.91Ω at 37° C. The current in the RTD is nominally 193 μA. A 1° C. increase gives a change of 1.932Ω in the value of the RTD, corresponding to a voltage change of about 360 μV on a DC level of about 110 mV.

With transistor Q1 off and Q2 on, current flows "downwards" through the RTD, 130. With Q1 on and Q2 off, current flows "upwards". Thus by acquiring the voltage at the analogue to digital converter (ADC), 131, under both conditions and adding them digitally, any DC offset in the circuit and any standing current in the RTD leads is eliminated.

Low pass RC filters (R1, C1 and R2, C2) reduce the effect of high frequency noise due to MRI RF and gradient coils. The ADC, 131, is a 16-bit sigma delta device with a programmed input gain of 8 so that 1 LSB corresponds to about 5.7 μV.

Typically, the temperature change due to RF heating and like effects is relatively slow (in the order of a few seconds or minutes) and therefore the sample acquisition rate for temperature readings may typically be less than 10 Hz. Digital filtering in the ADC is used to remove any noise in the 50 Hz and 60 Hz region caused by mains electrical supplies.

Other types of temperature sensors are possible such as other RTD materials or thermocouples. The platinum RTD is preferred because of long term stability, relative sensitivity and biocompatibility.

As mentioned above, the stimulator system is able to sense electromagnetically induced currents in the stimulator leads, this data being transmitted to the MRI operator. Due to electro-magnetic interference, intermediate storage and/or an error correcting wireless transmission protocol is required. The information may be used by the operator to position the patient in the field so that coupling between the MRI system and the stimulator leads is minimised. Furthermore, in leads not adapted for temperature measurement, the stimulator device may provide a limited form of protection for the patient by monitoring the level of electrical noise on the lead system and alerting the MRI operator if this exceeds limits that are known to cause electrode heating.

In an implanted system, an embodiment of the invention comprises the elements described below.

A programming system, with a graphical user interface, provides users and surgeons with an easy to use method of controlling the location and area of coverage of desired stimulus pulse with respect to an array of eight or sixteen electrodes. The user interface provides of a method of normalisation of sensation between electrodes. This may be achieved by slowly increasing the stimulus output on a subset of the electrodes, one electrode at a time, until the user reports first sensation. This data may then be automatically interpolated to derive data for all electrodes.

The transformation element in the controller has as its input the desired location and focus of the stimulus pulse from the graphical user interface and takes account of normalisation data to calculate the respective duty cycle and electrode pairing for a series of trains of sub-component pulses. The pulses should have a resolution on their duration of preferably 0.1 μs or better, such that by varying the respective duty cycles, the perceived stimulation on the electrode array can be controlled accurately and moved smoothly around the array. Preferably the sub-component pulses are constant current pulses of maximum duration of 10 μs or less and minimum duration of 0.5 μs or less. Preferably, during configuration of the stimulation patterns, the component pulse data is transmitted in real time over the MICS wireless channel to the implant, so that the user can report to the surgeon as he adjusts the stimulation field.

The implant preferably has a rechargeable battery which supplies a variable voltage switch mode supply, which feeds a high bandwidth analogue current source. This is turn supplies a series of 34 output switches that allow any of 16 electrodes and the stimulator case to be connected to the supply or to ground. The output switches should be high speed devices capable of producing component pulses of minimum 0.5 μs duration or less, of maximum amplitude 20 mA and maximum voltage 20V. A microprocessor coupled with a high-speed programmable logic device controls the switching matrix, synthesizing the sub-component pulses as commanded. To facilitate real-time update of the stimulation pattern, the microprocessor may implement a copy of the transformation element from the programming system, thereby deriving the sub-component pulses internally by interpolation from table based reference data on the basis of high-level information describing the parameters of the electrode array and desired stimulus pulse. Preferably, the sub-component pulses are delivered in sequence, so that they do not overlap but may have a space between each pulse of zero to up to 20 μs.

REFERENCES

Johnson M I, Ashton C H, Thompson J W (1991) An in-depth study of long-term users of transcutaneous electrical stimulation (TENS). Implications for clinical use of TENS. Pain 44:221-229.

Macdonald A J R, Coates T W (1995) The discovery of transcutaneous spinal electroanalgesia and its relief of chronic pain. Physiotherapy 81:653-661.

Melzack R, Wall P D (1965) Pain Mechanisms: a new theory. Science 150:971-979.

Palmer S T, Martin D J, Steedman W M, Ravey J (1999) Alteration of interferential current and transcutaneous electrical nerve stimulation frequency: effects on nerve excitation. Arch Phys Med Rehabil 80: 1065-1071.

Radhakrishnan R, Sluka K A (2005) Deep tissue afferents, but not cutaneous afferents, mediate TENS-induced antihyperalgesia. J Pain 10:673-680.

Salar G, Job I, Mingrino S, Bosio A, Trabucchi M (1981) Effect of transcutaneous electrotherapy on CSF β-endorphin content in patients without pain problems. Pain 10:169-172.

Shealy C N, Mortimer J T, Reswick J B (1967) Electrical inhibition of pain by stimulation of the dorsal columns: preliminary clinical report. Anesthesia & Analgesia 46:489-491.

Shealy C N, Mortimer J T (1971) Dorsal column electroanalgesia. In: (Eds) Reynolds D V, Sjoberg A E. Neuroelectric Research. Charles C Thomas. pp 146-150.

Wall PD (1986) The discovery of Transcutaneous Electrical Nerve Stimulation. Journal of Orthopaedic Medicine 3: 26-28.

The invention claimed is:

1. An apparatus for applying electrical pulses to a patient, the apparatus being implantable in the patient, the apparatus comprising a plurality of electrodes arranged in an array, the electrodes forming a plurality of electrode pairs wherein each pair comprises an anode and a cathode which are made up of one or more electrodes from the array electrically connected in parallel, and a signal generator for generating signals to said electrodes so as to form said electrical pulses, the signal generator being arranged to generate said signals such that the signals are either sequentially transmitted to successive electrode pairs in a cycle so the respective electrode pairs receive the corresponding signals at different times, or alternatively so that the signals are received by the electrode pairs such that they do not all start and end at the same point in time, wherein said electrical pulses form by addition a composite pulse which has a duration between 4 μs and 1500 μs and a maximum voltage between 2 v and 50 v, wherein the composite pulse comprises a plurality of said electrical pulses having a first polarity, and a subsequent plurality of said electrical pulses having a second polarity opposite to the first polarity.

2. An apparatus according to claim 1, wherein the signal generator is arranged to generate said signals such that, throughout the duration of said composite pulse, successive electrode pairs receive the corresponding signals.

3. An apparatus according to claim 1, wherein the signal generator is arranged to generate said signals such that there are gaps between said signals of a duration not greater than 200 μs during said composite pulse.

4. An apparatus according to claim 1, wherein said signal generator is arranged to generate said signals such that said signals are each pulse trains with a minimum pulse width of 0.1 μs and a maximum pulse width of 50 μs.

5. An apparatus according to claim 1, wherein said composite pulse has a duration between 20 μs and 1000 μs.

6. An apparatus according to claim 1, wherein said signal generator has a housing forming one of said electrodes.

7. An apparatus according to claim 1, wherein said signal generator has a plurality of signal generation devices, each signal generation device being associated with a corresponding one of said plurality of electrodes.

8. An apparatus according to claim 1, wherein said signal generator has at least one signal generation device and a network of high speed switching elements, the network of switching elements being arranged to direct the output of said at least one generation device to said electrode pairs.

9. An apparatus according to claim 1, wherein the signal generator is arranged to generate said signals such that said composite pulse has a notional pulse width and a notional voltage, current or charge, and which is arranged to generate a stimulation field of a desired location and area in the patient.

10. An apparatus according to claim 9, wherein said signal generator is arranged to control the relative duty signals of said signals, so as to vary said desired location and/area.

11. An apparatus according to claim 10, wherein said signal generator is further arranged to control the number, distribution and/or configuration of electrode pairs receiving said corresponding signals.

12. An apparatus according to claim 10, having an operator interface for controlling said signal generator so as to vary said desired location and/area.

13. An apparatus according to claim 1, wherein each of the said signals comprises a plurality of sub-components.

14. An apparatus according to claim 13, where the signal generator is arranged to separate said sub-components such that there are gaps between said sub-components and further gaps between said electrical pulses, said gaps and said further gaps each having a duration not greater than 200 μs, and the sum of the durations of said subcomponents, excluding said gaps and said further gaps, equal to the duration of said composite pulse.

15. An apparatus according to claim 1, wherein said signal generator is arranged to generate said signals such that said electrical pulses have a maximum pulse width of 10 μs.

16. An apparatus according to claim 14, wherein said electrical pulses have a maximum pulse width of 2 μs.

17. An apparatus according to claim 1, wherein said composite pulse has a duration between 20 μs and 1000 μs.

18. An apparatus according to claim 1, wherein the signal generator includes a power supply, a controller arranged to generate a composite signal corresponding to said composite pulse, and a converter arranged to convert the composite signal into said signals using a network of high speed switching elements.

19. An apparatus according to claim 1, wherein the signal generator includes a power supply, a controller storing data representing said composite pulse, and a network of high speed switching elements, the controller being arranged to control the power supply and said switching elements so as to generate said signals.

20. An apparatus according to claim 1, having a controller arranged to control, represent or store a desired notional voltage, current, charge or energy distribution in a mathematical or empirically derived model of human or animal tissue in the region of the array, and said signal generator includes a transformation element arranged to reduce said notional voltage, current charge or energy distribution into said signals and a stimulator arranged to send said signals to the array of electrodes, said stimulator being arranged to transmit said signals sequentially to said electrodes at different times such that successive electrode pairs are arranged to generate said pulses in a cycle, or to transmit said signals so that said pulses do not all start and end at the same point in time.

21. An apparatus according to claim 20, wherein said controller includes an operator interface for selectively controlling said notional voltage, current charge or energy distribution.

22. An apparatus according to claim 1, wherein said signal generator is arranged to generate said signals such that said electrical pulses have little or no activation of afferent fibres but said composite pulse is sufficient to cause an action potential in such fibres.

23. An apparatus according to claim 1, wherein the signal generator is arranged to generate said signals such that the relative pulse widths and plurality of said electrical pulses vary with respect to each other.

24. An apparatus according to claim 1, wherein the signal generator is arranged to generate said signals such that the relative pulse widths of said electrical pulses are determined with respect to each other to normalize the sensation at each electrode.

* * * * *